United States Patent
Zheng et al.

(10) Patent No.: US 10,975,364 B2
(45) Date of Patent: Apr. 13, 2021

(54) MODIFIED PROTEIN AND METHOD FOR ALTERING GENOME OF CELL

(71) Applicant: City University of Hong Kong, Kowloon (HK)

(72) Inventors: Zongli Zheng, Kowloon (HK); Jiahai Shi, Singapore (SG); Yuanyan Tan, Shatin (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 16/552,034

(22) Filed: Aug. 27, 2019

(65) Prior Publication Data

US 2021/0062169 A1 Mar. 4, 2021

(51) Int. Cl.
*C12N 9/22* (2006.01)
*C12N 15/11* (2006.01)
*C12N 15/90* (2006.01)

(52) U.S. Cl.
CPC ........... *C12N 9/22* (2013.01); *C12N 15/11* (2013.01); *C12N 15/902* (2013.01); *C12N 2310/20* (2017.05); *C12N 2800/80* (2013.01)

(58) Field of Classification Search
CPC ........ C12N 9/22; C12N 15/11; C12N 15/902; C12N 2310/20; C12N 2800/80
See application file for complete search history.

(56) References Cited

U.S. PATENT DOCUMENTS

2019/0071657 A1 3/2019 Joung et al.

OTHER PUBLICATIONS

Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for improving enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*

* cited by examiner

*Primary Examiner* — Ganapathirama Raghu
(74) *Attorney, Agent, or Firm* — Renner Kenner Greive Bobak Taylor & Weber

(57) ABSTRACT

A modified *Streptococcus aureus* Cas9 (SaCas9) protein with a mutation at an N413 position, and optionally one or more of a nuclear localization sequence, a cell penetrating peptide sequence, an affinity tag and/or a fusion base editor protein, and a kit that comprises said modified protein. A method for altering the genome of a cell, the method including the step of using the modified protein of the invention.

28 Claims, 19 Drawing Sheets
(7 of 19 Drawing Sheet(s) Filed in Color)

Specification includes a Sequence Listing.

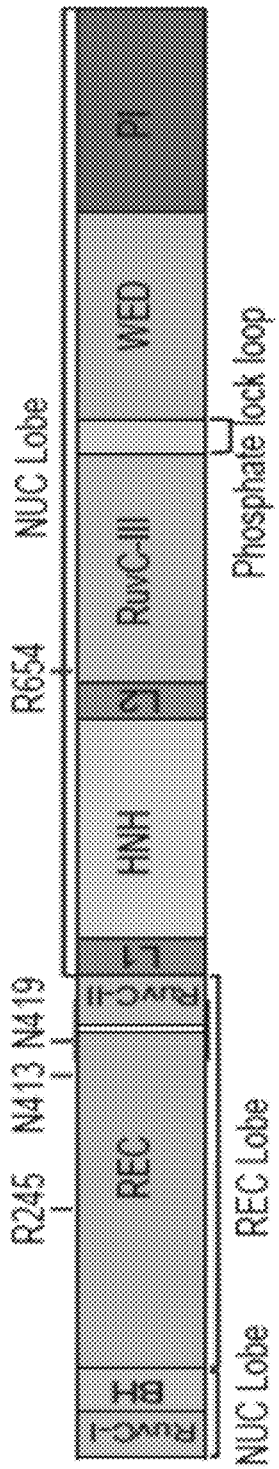
Figure 1C
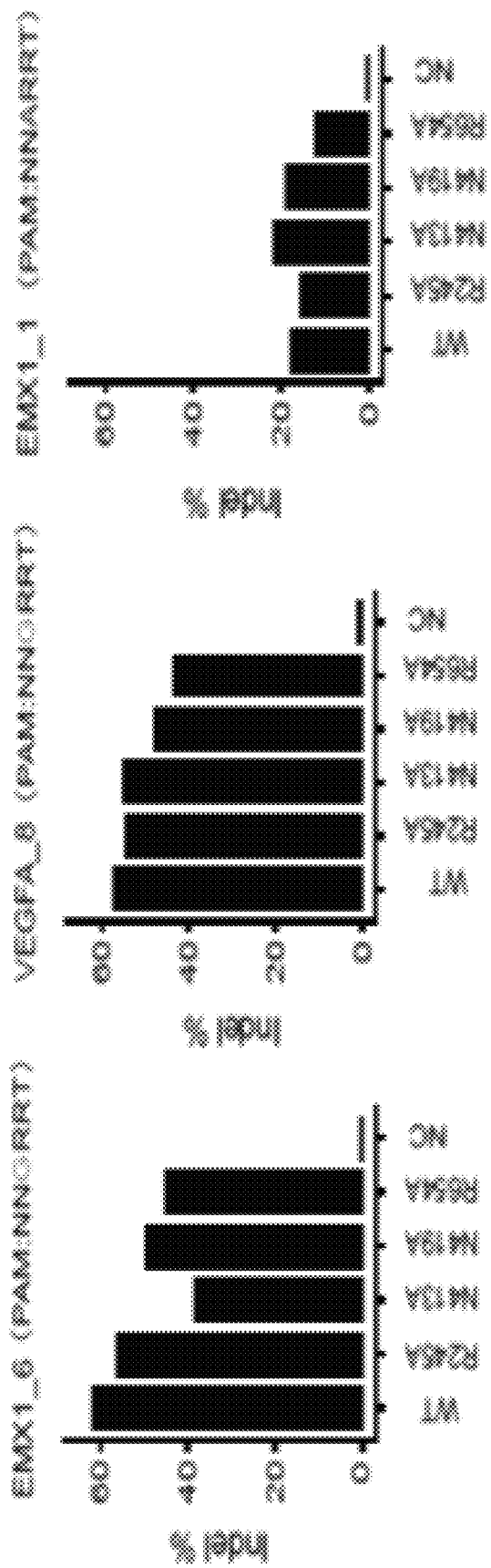
Figure 1D
Figure 1E
Figure 1F

SEQUENCE LISTING

```
<160> NUMBER OF SEQ ID NOS: 180

<210> SEQ ID NO 1
<211> LENGTH: 1086
<212> TYPE: PRT
<213> ORGANISM: Artificial Sequence
<220> FEATURE:
<223> OTHER INFORMATION: Synthesized

<400> SEQUENCE: 1

Gly Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205
```

```
Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Ala Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
```

-continued

```
            625                 630                 635                 640
        Phe Ile Asn Arg Asn Leu Val Asp Thr Arg Tyr Ala Thr Arg Gly Leu
                        645                 650                 655

Met Asn Leu Leu Arg Ser Tyr Phe Arg Val Asn Asn Leu Asp Val Lys
                        660                 665                 670

Val Lys Ser Ile Asn Gly Gly Phe Thr Ser Phe Leu Arg Arg Lys Trp
                        675                 680                 685

Lys Phe Lys Lys Glu Arg Asn Lys Gly Tyr Lys His His Ala Glu Asp
                        690                 695                 700

Ala Leu Ile Ile Ala Asn Ala Asp Phe Ile Phe Lys Glu Trp Lys Lys
        705                 710                 715                 720

Leu Asp Lys Ala Lys Lys Val Met Glu Asn Gln Met Phe Glu Glu Lys
                        725                 730                 735

Gln Ala Glu Ser Met Pro Glu Ile Glu Thr Gln Glu Tyr Lys Glu
                        740                 745                 750

Ile Phe Ile Thr Pro His Gln Ile Lys His Ile Lys Asp Phe Lys Asp
                        755                 760                 765

Tyr Lys Tyr Ser His Arg Val Asp Lys Lys Pro Asn Arg Glu Leu Ile
                        770                 775                 780

Asn Asp Thr Leu Tyr Ser Thr Arg Lys Asp Asp Lys Gly Asn Thr Leu
        785                 790                 795                 800

Ile Val Asn Asn Leu Asn Gly Leu Tyr Asp Lys Asp Asn Asp Lys Leu
                        805                 810                 815

Lys Lys Leu Ile Asn Lys Ser Pro Glu Lys Leu Leu Met Tyr His His
                        820                 825                 830

Asp Pro Gln Thr Tyr Gln Lys Leu Lys Leu Ile Met Glu Gln Tyr Gly
                        835                 840                 845

Asp Glu Lys Asn Pro Leu Tyr Lys Tyr Tyr Glu Glu Thr Gly Asn Tyr
                        850                 855                 860

Leu Thr Lys Tyr Ser Lys Lys Asp Asn Gly Pro Val Ile Lys Lys Ile
        865                 870                 875                 880

Lys Tyr Tyr Gly Asn Lys Leu Asn Ala His Leu Asp Ile Thr Asp Asp
                        885                 890                 895

Tyr Pro Asn Ser Arg Asn Lys Val Val Lys Leu Ser Leu Lys Pro Tyr
                        900                 905                 910

Arg Phe Asp Val Tyr Leu Asp Asn Gly Val Tyr Lys Phe Val Thr Val
                        915                 920                 925

Lys Asn Leu Asp Val Ile Lys Lys Glu Asn Tyr Glu Val Asn Ser
                        930                 935                 940

Lys Cys Tyr Glu Glu Ala Lys Lys Leu Lys Lys Ile Ser Asn Gln Ala
        945                 950                 955                 960

Glu Phe Ile Ala Ser Phe Tyr Asn Asn Asp Leu Ile Lys Ile Asn Gly
                        965                 970                 975

Glu Leu Tyr Arg Val Ile Gly Val Asn Asn Asp Leu Leu Asn Arg Ile
                        980                 985                 990

Glu Val Asn Met Ile Asp Ile Thr  Tyr Arg Glu Tyr Leu  Glu Asn Met
                995                1000                1005

Asn Asp Lys Arg Pro Pro Arg  Ile Ile Lys Thr Ile  Ala Ser Lys
                1010                1015                1020

Thr Gln Ser Ile Lys Lys Tyr  Ser Thr Asp Ile Leu  Gly Asn Leu
                1025                1030                1035

Tyr Glu Val Lys Ser Lys Lys  His Pro Gln Ile Ile  Lys Lys Gly
                1040                1045                1050
```

```
Gly Ser  Pro Lys Lys Arg  Lys Val Ser Ser  Asp  Tyr Lys Asp
    1055             1060              1065

His Asp  Gly Asp Tyr Lys  Asp His Asp Ile  Asp  Tyr Lys Asp Asp
1070             1075              1080

Asp Asp  Lys
    1085
```

<210> SEQ ID NO 2
<211> LENGTH: 1086
<212> TYPE: PRT
<213> ORGANISM: Artificial Sequence
<220> FEATURE:
<223> OTHER INFORMATION: Synthesized

<400> SEQUENCE: 2

```
Gly Lys Arg Asn Tyr Ile Leu Gly Leu Asp Ile Gly Ile Thr Ser Val
1               5                  10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320
```

Pro Glu Phe Thr Asn Leu Lys Val Tyr His Asp Ile Lys Asp Ile Thr
                    325                 330                 335

Ala Arg Lys Glu Ile Ile Glu Asn Ala Glu Leu Leu Asp Gln Ile Ala
                340                 345                 350

Lys Ile Leu Thr Ile Tyr Gln Ser Ser Glu Asp Ile Gln Glu Glu Leu
                355                 360                 365

Thr Asn Leu Asn Ser Glu Leu Thr Gln Glu Glu Ile Glu Gln Ile Ser
            370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Ala Gln Ile Ala
                405                 410                 415

Ile Phe Asn Arg Leu Lys Leu Val Pro Lys Lys Val Asp Leu Ser Gln
                420                 425                 430

Gln Lys Glu Ile Pro Thr Thr Leu Val Asp Asp Phe Ile Leu Ser Pro
            435                 440                 445

Val Val Lys Arg Ser Phe Ile Gln Ser Ile Lys Val Ile Asn Ala Ile
        450                 455                 460

Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
                500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
                580                 585                 590

Ser Ser Ser Asp Ser Lys Ile Ser Tyr Glu Thr Phe Lys Lys His Ile
            595                 600                 605

Leu Asn Leu Ala Lys Gly Lys Gly Arg Ile Ser Lys Thr Lys Lys Glu
        610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
            675                 680                 685

Lys Phe Lys Lys Glu Arg Asn Lys Gly Tyr Lys His His Ala Glu Asp
        690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

```
Gln Ala Glu Ser Met Pro Glu Ile Glu Thr Gln Glu Tyr Lys Glu
            740                 745                 750
Ile Phe Ile Thr Pro His Gln Ile Lys His Ile Lys Asp Phe Lys Asp
        755                 760                 765
Tyr Lys Tyr Ser His Arg Val Asp Lys Lys Pro Asn Arg Lys Leu Ile
    770                 775                 780
Asn Asp Thr Leu Tyr Ser Thr Arg Lys Asp Asp Lys Gly Asn Thr Leu
785                 790                 795                 800
Ile Val Asn Asn Leu Asn Gly Leu Tyr Asp Lys Asp Asn Asp Lys Leu
            805                 810                 815
Lys Lys Leu Ile Asn Lys Ser Pro Glu Lys Leu Leu Met Tyr His His
        820                 825                 830
Asp Pro Gln Thr Tyr Gln Lys Leu Lys Leu Ile Met Glu Gln Tyr Gly
    835                 840                 845
Asp Glu Lys Asn Pro Leu Tyr Lys Tyr Tyr Glu Glu Thr Gly Asn Tyr
    850                 855                 860
Leu Thr Lys Tyr Ser Lys Lys Asp Asn Gly Pro Val Ile Lys Lys Ile
865                 870                 875                 880
Lys Tyr Tyr Gly Asn Lys Leu Asn Ala His Leu Asp Ile Thr Asp Asp
            885                 890                 895
Tyr Pro Asn Ser Arg Asn Lys Val Val Lys Leu Ser Leu Lys Pro Tyr
        900                 905                 910
Arg Phe Asp Val Tyr Leu Asp Asn Gly Val Tyr Lys Phe Val Thr Val
    915                 920                 925
Lys Asn Leu Asp Val Ile Lys Lys Glu Asn Tyr Tyr Glu Val Asn Ser
930                 935                 940
Lys Cys Tyr Glu Glu Ala Lys Lys Leu Lys Lys Ile Ser Asn Gln Ala
945                 950                 955                 960
Glu Phe Ile Ala Ser Phe Tyr Lys Asn Asp Leu Ile Lys Ile Asn Gly
            965                 970                 975
Glu Leu Tyr Arg Val Ile Gly Val Asn Asn Asp Leu Leu Asn Arg Ile
        980                 985                 990
Glu Val Asn Met Ile Asp Ile Thr Tyr Arg Glu Tyr Leu Glu Asn Met
    995                 1000                1005
Asn Asp Lys Arg Pro Pro His Ile Ile Lys Thr Ile Ala Ser Lys
    1010                1015                1020
Thr Gln Ser Ile Lys Lys Tyr Ser Thr Asp Ile Leu Gly Asn Leu
    1025                1030                1035
Tyr Glu Val Lys Ser Lys Lys His Pro Gln Ile Ile Lys Lys Gly
    1040                1045                1050
Gly Ser Pro Lys Lys Arg Lys Val Ser Ser Asp Tyr Lys Asp
    1055                1060                1065
His Asp Gly Asp Tyr Lys Asp His Asp Ile Asp Tyr Lys Asp Asp
    1070                1075                1080
Asp Asp Lys
    1085

<210> SEQ ID NO 3
<211> LENGTH: 1086
<212> TYPE: PRT
<213> ORGANISM: Artificial Sequence
<220> FEATURE:
<223> OTHER INFORMATION: Synthesized

<400> SEQUENCE: 3
```

-continued

```
Gly Lys Arg Asn Tyr Ile Leu Gly Leu Asp Ile Gly Ile Thr Ser Val
1               5                   10                  15
Gly Tyr Gly Ile Ile Asp Tyr Glu Thr Arg Asp Val Ile Asp Ala Gly
                20                  25                  30
Val Arg Leu Phe Lys Glu Ala Asn Val Glu Asn Asn Glu Gly Arg Arg
                35                  40                  45
Ser Lys Arg Gly Ala Arg Arg Leu Lys Arg Arg Arg His Arg Ile
    50                  55                  60
Gln Arg Val Lys Lys Leu Leu Phe Asp Tyr Asn Leu Leu Thr Asp His
65                  70                  75                  80
Ser Glu Leu Ser Gly Ile Asn Pro Tyr Glu Ala Arg Val Lys Gly Leu
                85                  90                  95
Ser Gln Lys Leu Ser Glu Glu Phe Ser Ala Ala Leu Leu His Leu
                100                 105                 110
Ala Lys Arg Arg Gly Val His Asn Val Asn Glu Val Glu Glu Asp Thr
                115                 120                 125
Gly Asn Glu Leu Ser Thr Lys Glu Gln Ile Ser Arg Asn Ser Lys Ala
                130                 135                 140
Leu Glu Glu Lys Tyr Val Ala Glu Leu Gln Leu Glu Arg Leu Lys Lys
145                 150                 155                 160
Asp Gly Glu Val Arg Gly Ser Ile Asn Arg Phe Lys Thr Ser Asp Tyr
                165                 170                 175
Val Lys Glu Ala Lys Gln Leu Leu Lys Val Gln Lys Ala Tyr His Gln
                180                 185                 190
Leu Asp Gln Ser Phe Ile Asp Thr Tyr Ile Asp Leu Leu Glu Thr Arg
                195                 200                 205
Arg Thr Tyr Tyr Glu Gly Pro Gly Glu Gly Ser Pro Phe Gly Trp Lys
210                 215                 220
Asp Ile Lys Glu Trp Tyr Glu Met Leu Met Gly His Cys Thr Tyr Phe
225                 230                 235                 240
Pro Glu Glu Leu Ala Ser Val Lys Tyr Ala Tyr Asn Ala Asp Leu Tyr
                245                 250                 255
Asn Ala Leu Asn Asp Leu Asn Asn Leu Val Ile Thr Arg Asp Glu Asn
                260                 265                 270
Glu Lys Leu Glu Tyr Tyr Glu Lys Phe Gln Ile Ile Glu Asn Val Phe
                275                 280                 285
Lys Gln Lys Lys Lys Pro Thr Leu Lys Gln Ile Ala Lys Glu Ile Leu
                290                 295                 300
Val Asn Glu Glu Asp Ile Lys Gly Tyr Arg Val Thr Ser Thr Gly Lys
305                 310                 315                 320
Pro Glu Phe Thr Asn Leu Lys Val Tyr His Asp Ile Lys Asp Ile Thr
                325                 330                 335
Ala Arg Lys Glu Ile Ile Glu Asn Ala Glu Leu Leu Asp Gln Ile Ala
                340                 345                 350
Lys Ile Leu Thr Ile Tyr Gln Ser Ser Glu Asp Ile Gln Glu Glu Leu
                355                 360                 365
Thr Asn Leu Asn Ser Glu Leu Thr Gln Glu Glu Ile Glu Gln Ile Ser
                370                 375                 380
Asn Leu Lys Gly Tyr Thr Gly Thr His Asn Leu Ser Leu Lys Ala Ile
385                 390                 395                 400
Asn Leu Ile Leu Asp Glu Leu Trp His Thr Asn Asp Ala Gln Ile Ala
                405                 410                 415
Ile Phe Ala Arg Leu Lys Leu Val Pro Lys Lys Val Asp Leu Ser Gln
```

```
                420               425                430
    Gln Lys Glu Ile Pro Thr Thr Leu Val Asp Asp Phe Ile Leu Ser Pro
                    435                 440                 445
    Val Val Lys Arg Ser Phe Ile Gln Ser Ile Lys Val Ile Asn Ala Ile
                    450                 455                 460
    Ile Lys Lys Tyr Gly Leu Pro Asn Asp Ile Ile Glu Leu Ala Arg
    465                 470                 475                 480
    Glu Lys Asn Ser Lys Asp Ala Gln Lys Met Ile Asn Glu Met Gln Lys
                    485                 490                 495
    Arg Asn Arg Gln Thr Asn Glu Arg Ile Glu Glu Ile Arg Thr Thr
                    500                 505                 510
    Gly Lys Glu Asn Ala Lys Tyr Leu Ile Glu Lys Ile Lys Leu His Asp
                    515                 520                 525
    Met Gln Glu Gly Lys Cys Leu Tyr Ser Leu Glu Ala Ile Pro Leu Glu
                    530                 535                 540
    Asp Leu Leu Asn Asn Pro Phe Asn Tyr Glu Val Asp His Ile Ile Pro
    545                 550                 555                 560
    Arg Ser Val Ser Phe Asp Asn Ser Phe Asn Asn Lys Val Leu Val Lys
                    565                 570                 575
    Gln Glu Glu Asn Ser Lys Lys Gly Asn Arg Thr Pro Phe Gln Tyr Leu
                    580                 585                 590
    Ser Ser Ser Asp Ser Lys Ile Ser Tyr Glu Thr Phe Lys Lys His Ile
                    595                 600                 605
    Leu Asn Leu Ala Lys Gly Lys Gly Arg Ile Ser Lys Thr Lys Lys Glu
                    610                 615                 620
    Tyr Leu Leu Glu Glu Arg Asp Ile Asn Arg Phe Ser Val Gln Lys Asp
    625                 630                 635                 640
    Phe Ile Asn Arg Asn Leu Val Asp Thr Arg Tyr Ala Thr Ala Gly Leu
                    645                 650                 655
    Met Asn Leu Leu Arg Ser Tyr Phe Arg Val Asn Asn Leu Asp Val Lys
                    660                 665                 670
    Val Lys Ser Ile Asn Gly Gly Phe Thr Ser Phe Leu Arg Arg Lys Trp
                    675                 680                 685
    Lys Phe Lys Lys Glu Arg Asn Lys Gly Tyr Lys His His Ala Glu Asp
                    690                 695                 700
    Ala Leu Ile Ile Ala Asn Ala Asp Phe Ile Phe Lys Glu Trp Lys Lys
    705                 710                 715                 720
    Leu Asp Lys Ala Lys Lys Val Met Glu Asn Gln Met Phe Glu Glu Lys
                    725                 730                 735
    Gln Ala Glu Ser Met Pro Glu Ile Glu Thr Glu Gln Glu Tyr Lys Glu
                    740                 745                 750
    Ile Phe Ile Thr Pro His Gln Ile Lys His Ile Lys Asp Phe Lys Asp
                    755                 760                 765
    Tyr Lys Tyr Ser His Arg Val Asp Lys Lys Pro Asn Arg Glu Leu Ile
                    770                 775                 780
    Asn Asp Thr Leu Tyr Ser Thr Arg Lys Asp Asp Lys Gly Asn Thr Leu
    785                 790                 795                 800
    Ile Val Asn Asn Leu Asn Gly Leu Tyr Asp Lys Asp Asn Asp Lys Leu
                    805                 810                 815
    Lys Lys Leu Ile Asn Lys Ser Pro Glu Lys Leu Leu Met Tyr His His
                    820                 825                 830
    Asp Pro Gln Thr Tyr Gln Lys Leu Lys Leu Ile Met Glu Gln Tyr Gly
                    835                 840                 845
```

```
Asp Glu Lys Asn Pro Leu Tyr Lys Tyr Tyr Glu Thr Gly Asn Tyr
        850                 855                 860

Leu Thr Lys Tyr Ser Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
                900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
        930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
                980                 985                 990

Glu Val Asn Met Ile Asp Ile Thr Tyr Arg Glu Tyr Leu Glu Asn Met
        995                 1000                1005

Asn Asp Lys Arg Pro Pro Arg Ile Ile Lys Thr Ile Ala Ser Lys
        1010                1015                1020

Thr Gln Ser Ile Lys Lys Tyr Ser Thr Asp Ile Leu Gly Asn Leu
        1025                1030                1035

Tyr Glu Val Lys Ser Lys Lys His Pro Gln Ile Ile Lys Lys Gly
        1040                1045                1050

Gly Ser Pro Lys Lys Lys Arg Lys Val Ser Ser Asp Tyr Lys Asp
        1055                1060                1065

His Asp Gly Asp Tyr Lys Asp His Asp Ile Asp Tyr Lys Asp Asp
        1070                1075                1080

Asp Asp Lys
        1085

<210> SEQ ID NO 4
<211> LENGTH: 1086
<212> TYPE: PRT
<213> ORGANISM: Artificial Sequence
<220> FEATURE:
<223> OTHER INFORMATION: Synthesized

<400> SEQUENCE: 4

Gly Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
                100                 105                 110
```

```
Ala Lys Arg Arg Gly Val His Asn Val Asn Glu Val Glu Glu Asp Thr
        115                 120                 125
Gly Asn Glu Leu Ser Thr Lys Glu Gln Ile Ser Arg Asn Ser Lys Ala
    130                 135                 140
Leu Glu Glu Lys Tyr Val Ala Glu Leu Gln Leu Glu Arg Leu Lys Lys
145                 150                 155                 160
Asp Gly Glu Val Arg Gly Ser Ile Asn Arg Phe Lys Thr Ser Asp Tyr
                165                 170                 175
Val Lys Glu Ala Lys Gln Leu Leu Lys Val Gln Lys Ala Tyr His Gln
                180                 185                 190
Leu Asp Gln Ser Phe Ile Asp Thr Tyr Ile Asp Leu Leu Glu Thr Arg
        195                 200                 205
Arg Thr Tyr Tyr Glu Gly Pro Gly Glu Gly Ser Pro Phe Gly Trp Lys
    210                 215                 220
Asp Ile Lys Glu Trp Tyr Glu Met Leu Met Gly His Cys Thr Tyr Phe
225                 230                 235                 240
Pro Glu Glu Leu Ala Ser Val Lys Tyr Ala Tyr Asn Ala Asp Leu Tyr
                245                 250                 255
Asn Ala Leu Asn Asp Leu Asn Asn Leu Val Ile Thr Arg Asp Glu Asn
        260                 265                 270
Glu Lys Leu Glu Tyr Tyr Glu Lys Phe Gln Ile Ile Glu Asn Val Phe
    275                 280                 285
Lys Gln Lys Lys Lys Pro Thr Leu Lys Gln Ile Ala Lys Glu Ile Leu
290                 295                 300
Val Asn Glu Glu Asp Ile Lys Gly Tyr Arg Val Thr Ser Thr Gly Lys
305                 310                 315                 320
Pro Glu Phe Thr Asn Leu Lys Val Tyr His Asp Ile Lys Asp Ile Thr
                325                 330                 335
Ala Arg Lys Glu Ile Ile Glu Asn Ala Glu Leu Leu Asp Gln Ile Ala
        340                 345                 350
Lys Ile Leu Thr Ile Tyr Gln Ser Ser Glu Asp Ile Gln Glu Glu Leu
    355                 360                 365
Thr Asn Leu Asn Ser Glu Leu Thr Gln Glu Glu Ile Glu Gln Ile Ser
    370                 375                 380
Asn Leu Lys Gly Tyr Thr Gly Thr His Asn Leu Ser Leu Lys Ala Ile
385                 390                 395                 400
Asn Leu Ile Leu Asp Glu Leu Trp His Thr Asn Asp Ala Gln Ile Ala
                405                 410                 415
Ile Phe Ala Arg Leu Lys Leu Val Pro Lys Lys Val Asp Leu Ser Gln
        420                 425                 430
Gln Lys Glu Ile Pro Thr Thr Leu Val Asp Asp Phe Ile Leu Ser Pro
    435                 440                 445
Val Val Lys Arg Ser Phe Ile Gln Ser Ile Lys Val Ile Asn Ala Ile
450                 455                 460
Ile Lys Lys Tyr Gly Leu Pro Asn Asp Ile Ile Glu Leu Ala Arg
465                 470                 475                 480
Glu Lys Asn Ser Lys Asp Ala Gln Lys Met Ile Asn Glu Met Gln Lys
                485                 490                 495
Arg Asn Arg Gln Thr Asn Glu Arg Ile Glu Glu Ile Ile Arg Thr Thr
        500                 505                 510
Gly Lys Glu Asn Ala Lys Tyr Leu Ile Glu Lys Ile Lys Leu His Asp
    515                 520                 525
```

```
Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Ala Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Lys Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Glu Val Asn Ser
    930                 935                 940

Lys Cys Tyr Glu Glu Ala Lys Lys Leu Lys Lys Ile Ser Asn Gln Ala
```

```
                    945                 950                 955                 960
              Glu Phe Ile Ala Ser Phe Tyr Lys Asn Asp Leu Ile Lys Ile Asn Gly
                              965                 970                 975

Glu Leu Tyr Arg Val Ile Gly Val Asn Asn Asp Leu Leu Asn Arg Ile
                              980                 985                 990

Glu Val Asn Met Ile Asp Ile Thr  Tyr Arg Glu Tyr Leu  Glu Asn Met
                       995                 1000                1005

Asn Asp  Lys Arg Pro Pro His  Ile Ile Lys Thr Ile  Ala Ser Lys
                       1010                1015                1020

Thr Gln  Ser Ile Lys Lys Tyr  Ser Thr Asp Ile Leu  Gly Asn Leu
                       1025                1030                1035

Tyr Glu  Val Lys Ser Lys Lys  His Pro Gln Ile  Lys Lys Gly
                       1040                1045                1050

Gly Ser  Pro Lys Lys Lys Arg  Lys Val Ser Ser Asp  Tyr Lys Asp
                       1055                1060                1065

His Asp  Gly Asp Tyr Lys Asp  His Asp Ile Asp Tyr  Lys Asp Asp
                       1070                1075                1080

Asp Asp  Lys
                       1085

<210> SEQ ID NO 5
<211> LENGTH: 26
<212> TYPE: DNA
<213> ORGANISM: Artificial Sequence
<220> FEATURE:
<223> OTHER INFORMATION: Synthesized

<400> SEQUENCE: 5
caaggcgagg agctgttcac cggggt                                          26

<210> SEQ ID NO 6
<211> LENGTH: 26
<212> TYPE: DNA
<213> ORGANISM: Artificial Sequence
<220> FEATURE:
<223> OTHER INFORMATION: Synthesized

<400> SEQUENCE: 6
caaggcgagg agctgttctg cggggt                                          26

<210> SEQ ID NO 7
<211> LENGTH: 26
<212> TYPE: DNA
<213> ORGANISM: Artificial Sequence
<220> FEATURE:
<223> OTHER INFORMATION: Synthesized

<400> SEQUENCE: 7
caaggcgagg agctgttagc cggggt                                          26

<210> SEQ ID NO 8
<211> LENGTH: 26
<212> TYPE: DNA
<213> ORGANISM: Artificial Sequence
<220> FEATURE:
<223> OTHER INFORMATION: Synthesized

<400> SEQUENCE: 8
caaggcgagg agctgcacac cggggt                                          26

<210> SEQ ID NO 9
```

```
<211> LENGTH: 26
<212> TYPE: DNA
<213> ORGANISM: Artificial Sequence
<220> FEATURE:
<223> OTHER INFORMATION: Synthesized

<400> SEQUENCE: 9
caaggcgagg agcgattcac cggggt                                          26

<210> SEQ ID NO 10
<211> LENGTH: 26
<212> TYPE: DNA
<213> ORGANISM: Artificial Sequence
<220> FEATURE:
<223> OTHER INFORMATION: Synthesized

<400> SEQUENCE: 10
caaggcgagg atctgttcac cggggt                                          26

<210> SEQ ID NO 11
<211> LENGTH: 26
<212> TYPE: DNA
<213> ORGANISM: Artificial Sequence
<220> FEATURE:
<223> OTHER INFORMATION: Synthesized

<400> SEQUENCE: 11
caaggcgagc cgctgttcac cggggt                                          26

<210> SEQ ID NO 12
<211> LENGTH: 26
<212> TYPE: DNA
<213> ORGANISM: Artificial Sequence
<220> FEATURE:
<223> OTHER INFORMATION: Synthesized

<400> SEQUENCE: 12
caaggcgctg agctgttcac cggggt                                          26

<210> SEQ ID NO 13
<211> LENGTH: 26
<212> TYPE: DNA
<213> ORGANISM: Artificial Sequence
<220> FEATURE:
<223> OTHER INFORMATION: Synthesized

<400> SEQUENCE: 13
caaggcgagg agctgttcac cggggt                                          26

<210> SEQ ID NO 14
<211> LENGTH: 26
<212> TYPE: DNA
<213> ORGANISM: Artificial Sequence
<220> FEATURE:
<223> OTHER INFORMATION: Synthesized

<400> SEQUENCE: 14
caacccgagg agctgttcac cggggt                                          26

<210> SEQ ID NO 15
<211> LENGTH: 26
<212> TYPE: DNA
<213> ORGANISM: Artificial Sequence
<220> FEATURE:
<223> OTHER INFORMATION: Synthesized

<400> SEQUENCE: 15
```

```
cttggcgagg agctgttcac cggggt                                              26

<210> SEQ ID NO 16
<211> LENGTH: 26
<212> TYPE: DNA
<213> ORGANISM: Artificial Sequence
<220> FEATURE:
<223> OTHER INFORMATION: Synthesized

<400> SEQUENCE: 16
gtaggcgagg agctgttcac cggggt                                              26

<210> SEQ ID NO 17
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 17
gcaaccacaa acccacgagg gnngrrt                                             27

<210> SEQ ID NO 18
<211> LENGTH: 27
<212> TYPE: DNA
<213> ORGANISM: Artificial Sequence
<220> FEATURE:
<223> OTHER INFORMATION: Synthesized

<400> SEQUENCE: 18
gcaaccacaa acccacgagg gcagagt                                             27

<210> SEQ ID NO 19
<211> LENGTH: 27
<212> TYPE: DNA
<213> ORGANISM: Artificial Sequence
<220> FEATURE:
<223> OTHER INFORMATION: Synthesized

<400> SEQUENCE: 19
acaaacacat acccacaagg acagagt                                             27

<210> SEQ ID NO 20
<211> LENGTH: 27
<212> TYPE: DNA
<213> ORGANISM: Artificial Sequence
<220> FEATURE:
<223> OTHER INFORMATION: Synthesized

<400> SEQUENCE: 20
gcaatcacaa taccacaagg gaagagg                                             27

<210> SEQ ID NO 21
<211> LENGTH: 27
<212> TYPE: DNA
<213> ORGANISM: Artificial Sequence
<220> FEATURE:
<223> OTHER INFORMATION: Synthesized

<400> SEQUENCE: 21
gcttccaccc agccacgaag gcagggt                                             27
```

<210> SEQ ID NO 22
<211> LENGTH: 27
<212> TYPE: DNA
<213> ORGANISM: Artificial Sequence
<220> FEATURE:
<223> OTHER INFORMATION: Synthesized

<400> SEQUENCE: 22
gccacccctc acccactagg ataccaa                                        27

<210> SEQ ID NO 23
<211> LENGTH: 27
<212> TYPE: DNA
<213> ORGANISM: Artificial Sequence
<220> FEATURE:
<223> OTHER INFORMATION: Synthesized

<400> SEQUENCE: 23
gccatcacac acccacgctt tgctgat                                        27

<210> SEQ ID NO 24
<211> LENGTH: 27
<212> TYPE: DNA
<213> ORGANISM: Artificial Sequence
<220> FEATURE:
<223> OTHER INFORMATION: Synthesized

<400> SEQUENCE: 24
acaaccacaa agccacaggg gtagagt                                        27

<210> SEQ ID NO 25
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 25
gggtgagtga gtgtgtgcgt gnngrrt                                        27

<210> SEQ ID NO 26
<211> LENGTH: 27
<212> TYPE: DNA
<213> ORGANISM: Artificial Sequence
<220> FEATURE:
<223> OTHER INFORMATION: Synthesized

<400> SEQUENCE: 26
gggtgagtga gtgtgtgcgt gtggggt                                        27

<210> SEQ ID NO 27
<211> LENGTH: 27
<212> TYPE: DNA
<213> ORGANISM: Artificial Sequence
<220> FEATURE:
<223> OTHER INFORMATION: Synthesized

<400> SEQUENCE: 27
gggtgagtca gtgtgtgagt ggagagt                                        27

<210> SEQ ID NO 28
<211> LENGTH: 27

```
<212> TYPE: DNA
<213> ORGANISM: Artificial Sequence
<220> FEATURE:
<223> OTHER INFORMATION: Synthesized

<400> SEQUENCE: 28
gagtgaatga gtgtgtgtgt gtggggt                                               27

<210> SEQ ID NO 29
<211> LENGTH: 27
<212> TYPE: DNA
<213> ORGANISM: Artificial Sequence
<220> FEATURE:
<223> OTHER INFORMATION: Synthesized

<400> SEQUENCE: 29
gggtgagtga gtgagtgagt ggtgagt                                               27

<210> SEQ ID NO 30
<211> LENGTH: 27
<212> TYPE: DNA
<213> ORGANISM: Artificial Sequence
<220> FEATURE:
<223> OTHER INFORMATION: Synthesized

<400> SEQUENCE: 30
gggtgagtca gtgagtgcgt ggtgagt                                               27

<210> SEQ ID NO 31
<211> LENGTH: 27
<212> TYPE: DNA
<213> ORGANISM: Artificial Sequence
<220> FEATURE:
<223> OTHER INFORMATION: Synthesized

<400> SEQUENCE: 31
gggtgagtca gtgtgtgagt ggtgagt                                               27

<210> SEQ ID NO 32
<211> LENGTH: 27
<212> TYPE: DNA
<213> ORGANISM: Artificial Sequence
<220> FEATURE:
<223> OTHER INFORMATION: Synthesized

<400> SEQUENCE: 32
gggtgagtca gtgagtgcgt gatgagt                                               27

<210> SEQ ID NO 33
<211> LENGTH: 27
<212> TYPE: DNA
<213> ORGANISM: Artificial Sequence
<220> FEATURE:
<223> OTHER INFORMATION: Synthesized

<400> SEQUENCE: 33
gagcgagtgg gtgtgtgcgt gggggt                                                27

<210> SEQ ID NO 34
<211> LENGTH: 27
<212> TYPE: DNA
<213> ORGANISM: Artificial Sequence
<220> FEATURE:
<223> OTHER INFORMATION: Synthesized

<400> SEQUENCE: 34
```
gagtgagtga gtgtgtgtgt gggggggg                    27

<210> SEQ ID NO 35
<211> LENGTH: 27
<212> TYPE: DNA
<213> ORGANISM: Artificial Sequence
<220> FEATURE:
<223> OTHER INFORMATION: Synthesized

<400> SEQUENCE: 35
gggtgagtca gtgtgtgggt ggtgagt                     27

<210> SEQ ID NO 36
<211> LENGTH: 27
<212> TYPE: DNA
<213> ORGANISM: Artificial Sequence
<220> FEATURE:
<223> OTHER INFORMATION: Synthesized

<400> SEQUENCE: 36
ggatgagtga gtgagtgagt ggggagt                     27

<210> SEQ ID NO 37
<211> LENGTH: 27
<212> TYPE: DNA
<213> ORGANISM: Artificial Sequence
<220> FEATURE:
<223> OTHER INFORMATION: Synthesized

<400> SEQUENCE: 37
gggtgagtga gtgagtgagt ggtgggt                     27

<210> SEQ ID NO 38
<211> LENGTH: 27
<212> TYPE: DNA
<213> ORGANISM: Artificial Sequence
<220> FEATURE:
<223> OTHER INFORMATION: Synthesized

<400> SEQUENCE: 38
gggtgtgtgt ctgtgtgcgt gtgggt                      27

<210> SEQ ID NO 39
<211> LENGTH: 27
<212> TYPE: DNA
<213> ORGANISM: Artificial Sequence
<220> FEATURE:
<223> OTHER INFORMATION: Synthesized

<400> SEQUENCE: 39
ggatgagtga gtgagtgcat gttgagt                     27

<210> SEQ ID NO 40
<211> LENGTH: 27
<212> TYPE: DNA
<213> ORGANISM: Artificial Sequence
<220> FEATURE:
<223> OTHER INFORMATION: Synthesized

<400> SEQUENCE: 40
gggtgagtga gtgagtgagt gagtggt                     27

<210> SEQ ID NO 41
<211> LENGTH: 27
<212> TYPE: DNA
<213> ORGANISM: Artificial Sequence
<220> FEATURE:
<223> OTHER INFORMATION: Synthesized

<400> SEQUENCE: 41
aggtgaccgt gtgtgtgcgt ggagggt                                          27

<210> SEQ ID NO 42
<211> LENGTH: 27
<212> TYPE: DNA
<213> ORGANISM: Artificial Sequence
<220> FEATURE:
<223> OTHER INFORMATION: Synthesized

<400> SEQUENCE: 42
gggtgagtca ctgtgtgagt ggtgagt                                          27

<210> SEQ ID NO 43
<211> LENGTH: 27
<212> TYPE: DNA
<213> ORGANISM: Artificial Sequence
<220> FEATURE:
<223> OTHER INFORMATION: Synthesized

<400> SEQUENCE: 43
gagtgagtga gtgagtgagt ggtgagt                                          27

<210> SEQ ID NO 44
<211> LENGTH: 27
<212> TYPE: DNA
<213> ORGANISM: Artificial Sequence
<220> FEATURE:
<223> OTHER INFORMATION: Synthesized

<400> SEQUENCE: 44
gggtgaaaga gtatgatggg gtggtgg                                          27

<210> SEQ ID NO 45
<211> LENGTH: 27
<212> TYPE: DNA
<213> ORGANISM: Artificial Sequence
<220> FEATURE:
<223> OTHER INFORMATION: Synthesized

<400> SEQUENCE: 45
gagtgagtga gtgagtgagt gatgaat                                          27

<210> SEQ ID NO 46
<211> LENGTH: 27
<212> TYPE: DNA
<213> ORGANISM: Artificial Sequence
<220> FEATURE:
<223> OTHER INFORMATION: Synthesized

<400> SEQUENCE: 46
aggtgagtga gtgtgtgtgt gttgggg                                          27

<210> SEQ ID NO 47
<211> LENGTH: 27
<212> TYPE: DNA
<213> ORGANISM: Artificial Sequence
<220> FEATURE:
<223> OTHER INFORMATION: Synthesized

<400> SEQUENCE: 47
gggtgagtga gtgagtgggt ggtgagt                                          27

<210> SEQ ID NO 48
<211> LENGTH: 27
<212> TYPE: DNA
<213> ORGANISM: Artificial Sequence
<220> FEATURE:
<223> OTHER INFORMATION: Synthesized

<400> SEQUENCE: 48
gaatgagtga gtgtgtgagt ggagaat                                       27

<210> SEQ ID NO 49
<211> LENGTH: 27
<212> TYPE: DNA
<213> ORGANISM: Artificial Sequence
<220> FEATURE:
<223> OTHER INFORMATION: Synthesized

<400> SEQUENCE: 49
gggtgagtga gtgagtgaga ggtgagt                                       27

<210> SEQ ID NO 50
<211> LENGTH: 27
<212> TYPE: DNA
<213> ORGANISM: Artificial Sequence
<220> FEATURE:
<223> OTHER INFORMATION: Synthesized

<400> SEQUENCE: 50
gggtgagtca gtgcgtgagt ggtgagt                                       27

<210> SEQ ID NO 51
<211> LENGTH: 27
<212> TYPE: DNA
<213> ORGANISM: Artificial Sequence
<220> FEATURE:
<223> OTHER INFORMATION: Synthesized

<400> SEQUENCE: 51
gtgtgagcgt gtgtgtgcgt ggagatg                                       27

<210> SEQ ID NO 52
<211> LENGTH: 27
<212> TYPE: DNA
<213> ORGANISM: Artificial Sequence
<220> FEATURE:
<223> OTHER INFORMATION: Synthesized

<400> SEQUENCE: 52
tggtgagtga gtgagtgagt gagtgag                                       27

<210> SEQ ID NO 53
<211> LENGTH: 27
<212> TYPE: DNA
<213> ORGANISM: Artificial Sequence
<220> FEATURE:
<223> OTHER INFORMATION: Synthesized

<400> SEQUENCE: 53
tggtgagtga gtgagtgagt gatgggt                                       27

<210> SEQ ID NO 54
<211> LENGTH: 27
<212> TYPE: DNA
<213> ORGANISM: Artificial Sequence
<220> FEATURE:
<223> OTHER INFORMATION: Synthesized -continued

```
<400> SEQUENCE: 54
gggtgagtga gtgagtgagt ggtgaat                              27

<210> SEQ ID NO 55
<211> LENGTH: 27
<212> TYPE: DNA
<213> ORGANISM: Artificial Sequence
<220> FEATURE:
<223> OTHER INFORMATION: Synthesized

<400> SEQUENCE: 55
gagtgagtca gtgtgtgagt ggtgagt                              27

<210> SEQ ID NO 56
<211> LENGTH: 27
<212> TYPE: DNA
<213> ORGANISM: Artificial Sequence
<220> FEATURE:
<223> OTHER INFORMATION: Synthesized

<400> SEQUENCE: 56
gggtgagtca gtgagtgagt gacgagt                              27

<210> SEQ ID NO 57
<211> LENGTH: 27
<212> TYPE: DNA
<213> ORGANISM: Artificial Sequence
<220> FEATURE:
<223> OTHER INFORMATION: Synthesized

<400> SEQUENCE: 57
gtgtgggtga gtgtgtgcgt gaggaca                              27

<210> SEQ ID NO 58
<211> LENGTH: 27
<212> TYPE: DNA
<213> ORGANISM: Artificial Sequence
<220> FEATURE:
<223> OTHER INFORMATION: Synthesized

<400> SEQUENCE: 58
gtgtgtgtga gtgtgtgtgt gtggggg                              27

<210> SEQ ID NO 59
<211> LENGTH: 27
<212> TYPE: DNA
<213> ORGANISM: Artificial Sequence
<220> FEATURE:
<223> OTHER INFORMATION: Synthesized

<400> SEQUENCE: 59
gggagagaga gagagagaga gagagag                              27

<210> SEQ ID NO 60
<211> LENGTH: 27
<212> TYPE: DNA
<213> ORGANISM: Artificial Sequence
<220> FEATURE:
<223> OTHER INFORMATION: Synthesized

<400> SEQUENCE: 60
gggagaggga gagggagaga gcttttt                              27

<210> SEQ ID NO 61
```

```
<211> LENGTH: 27
<212> TYPE: DNA
<213> ORGANISM: Artificial Sequence
<220> FEATURE:
<223> OTHER INFORMATION: Synthesized

<400> SEQUENCE: 61
gggagaggga gagggagagg gaactga                                              27

<210> SEQ ID NO 62
<211> LENGTH: 27
<212> TYPE: DNA
<213> ORGANISM: Artificial Sequence
<220> FEATURE:
<223> OTHER INFORMATION: Synthesized

<400> SEQUENCE: 62
gggagaggga gagggagagg gctatta                                              27

<210> SEQ ID NO 63
<211> LENGTH: 27
<212> TYPE: DNA
<213> ORGANISM: Artificial Sequence
<220> FEATURE:
<223> OTHER INFORMATION: Synthesized

<400> SEQUENCE: 63
gggtaagtga gtgagtgagt gagtggt                                              27

<210> SEQ ID NO 64
<211> LENGTH: 27
<212> TYPE: DNA
<213> ORGANISM: Artificial Sequence
<220> FEATURE:
<223> OTHER INFORMATION: Synthesized

<400> SEQUENCE: 64
gggtgagggg ttgtgggtgg agcttat                                              27

<210> SEQ ID NO 65
<211> LENGTH: 27
<212> TYPE: DNA
<213> ORGANISM: Artificial Sequence
<220> FEATURE:
<223> OTHER INFORMATION: Synthesized

<400> SEQUENCE: 65
gggtgggtag gtttgttggt atcctag                                              27

<210> SEQ ID NO 66
<211> LENGTH: 28
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (23)..(24)
<223> OTHER INFORMATION: n is a, c, g, t or u

<400> SEQUENCE: 66
gtgtggttcc agaaccggag gannarrt                                             28

<210> SEQ ID NO 67
<211> LENGTH: 28
<212> TYPE: DNA
<213> ORGANISM: Artificial Sequence
```

```
<220> FEATURE:
<223> OTHER INFORMATION: Synthesized

<400> SEQUENCE: 67
gtgtggttcc agaaccggag gacaaagt                                              28

<210> SEQ ID NO 68
<211> LENGTH: 28
<212> TYPE: DNA
<213> ORGANISM: Artificial Sequence
<220> FEATURE:
<223> OTHER INFORMATION: Synthesized

<400> SEQUENCE: 68
gtgtggttcc agaaccgaag gatgaagt                                              28

<210> SEQ ID NO 69
<211> LENGTH: 28
<212> TYPE: DNA
<213> ORGANISM: Artificial Sequence
<220> FEATURE:
<223> OTHER INFORMATION: Synthesized

<400> SEQUENCE: 69
atctggttcc agaaccggag gatgaagt                                              28

<210> SEQ ID NO 70
<211> LENGTH: 28
<212> TYPE: DNA
<213> ORGANISM: Artificial Sequence
<220> FEATURE:
<223> OTHER INFORMATION: Synthesized

<400> SEQUENCE: 70
gtgtggtttc agaaccggag gatgaagc                                              28

<210> SEQ ID NO 71
<211> LENGTH: 29
<212> TYPE: DNA
<213> ORGANISM: Artificial Sequence
<220> FEATURE:
<223> OTHER INFORMATION: Synthesized

<400> SEQUENCE: 71
atcgtggttc cagaaccgaa ggatgaagt                                             29

<210> SEQ ID NO 72
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 72
gcaaggcccg gcgcacggtg gnngrrt                                               27

<210> SEQ ID NO 73
<211> LENGTH: 27
<212> TYPE: DNA
<213> ORGANISM: Artificial Sequence
<220> FEATURE:
<223> OTHER INFORMATION: Synthesized
```

<400> SEQUENCE: 73
gcaaggcccg gcgcacggtg gcggggt					27

<210> SEQ ID NO 74
<211> LENGTH: 27
<212> TYPE: DNA
<213> ORGANISM: Artificial Sequence
<220> FEATURE:
<223> OTHER INFORMATION: Synthesized

<400> SEQUENCE: 74
gcaaggcctg gcccactgtg gcaggat					27

<210> SEQ ID NO 75
<211> LENGTH: 27
<212> TYPE: DNA
<213> ORGANISM: Artificial Sequence
<220> FEATURE:
<223> OTHER INFORMATION: Synthesized

<400> SEQUENCE: 75
gcaagggctg gggagcggtg ggaggaa					27

<210> SEQ ID NO 76
<211> LENGTH: 27
<212> TYPE: DNA
<213> ORGANISM: Artificial Sequence
<220> FEATURE:
<223> OTHER INFORMATION: Synthesized

<400> SEQUENCE: 76
gtaaggccaa gtacacagtg ggtgagt					27

<210> SEQ ID NO 77
<211> LENGTH: 27
<212> TYPE: DNA
<213> ORGANISM: Artificial Sequence
<220> FEATURE:
<223> OTHER INFORMATION: Synthesized

<400> SEQUENCE: 77
gcaaggccag gagcacgggt ggcagag					27

<210> SEQ ID NO 78
<211> LENGTH: 27
<212> TYPE: DNA
<213> ORGANISM: Artificial Sequence
<220> FEATURE:
<223> OTHER INFORMATION: Synthesized

<400> SEQUENCE: 78
ctgaggcccg gcccacggtg gtgagga					27

<210> SEQ ID NO 79
<211> LENGTH: 27
<212> TYPE: DNA
<213> ORGANISM: Artificial Sequence
<220> FEATURE:
<223> OTHER INFORMATION: Synthesized

<400> SEQUENCE: 79
acaaggctcg gcccacgggg gctgagg					27

<210> SEQ ID NO 80
<211> LENGTH: 27

<212> TYPE: DNA
<213> ORGANISM: Artificial Sequence
<220> FEATURE:
<223> OTHER INFORMATION: Synthesized

<400> SEQUENCE: 80
cagaggccag gcgcacggag agggagt                                27

<210> SEQ ID NO 81
<211> LENGTH: 27
<212> TYPE: DNA
<213> ORGANISM: Artificial Sequence
<220> FEATURE:
<223> OTHER INFORMATION: Synthesized

<400> SEQUENCE: 81
acaaggccag agacacagtt ggggagt                                27

<210> SEQ ID NO 82
<211> LENGTH: 27
<212> TYPE: DNA
<213> ORGANISM: Artificial Sequence
<220> FEATURE:
<223> OTHER INFORMATION: Synthesized

<400> SEQUENCE: 82
gctgggccag gagcacagtg gtggga                                 27

<210> SEQ ID NO 83
<211> LENGTH: 27
<212> TYPE: DNA
<213> ORGANISM: Artificial Sequence
<220> FEATURE:
<223> OTHER INFORMATION: Synthesized

<400> SEQUENCE: 83
acaaggctca gaacacggtg agaaagt                                27

<210> SEQ ID NO 84
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 84
gtagggcctt cgcgcacctc anngrrt                                27

<210> SEQ ID NO 85
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 85
gtagggcctt cgcgcacctc anngaat                                27

<210> SEQ ID NO 86

```
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 86
gaaagagaga tgtagggcta gnngrrt                                        27

<210> SEQ ID NO 87
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 87
gaaagagaga tgtagggcta gnngggt                                        27

<210> SEQ ID NO 88
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 88
gaaagaaagc tgcagggcaa gnngaat                                        27

<210> SEQ ID NO 89
<211> LENGTH: 29
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (24)..(25)
<223> OTHER INFORMATION: n is a, c, g, t or u

<400> SEQUENCE: 89
gtactcacct ctcatgaagc actnngrrt                                      29

<210> SEQ ID NO 90
<211> LENGTH: 29
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (24)..(25)
<223> OTHER INFORMATION: n is a, c, g, t or u

<400> SEQUENCE: 90
gtactcacct ctcatgaagc actnngggt                                      29
```

```
<210> SEQ ID NO 91
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 91
gctcagcctg agtgttgagg cnncrrt                                              27

<210> SEQ ID NO 92
<211> LENGTH: 27
<212> TYPE: DNA
<213> ORGANISM: Artificial Sequence
<220> FEATURE:
<223> OTHER INFORMATION: Synthesized

<400> SEQUENCE: 92
ctgcagactg agtgttaagg ccggagt                                              27

<210> SEQ ID NO 93
<211> LENGTH: 27
<212> TYPE: DNA
<213> ORGANISM: Artificial Sequence
<220> FEATURE:
<223> OTHER INFORMATION: Synthesized

<400> SEQUENCE: 93
cctcagcctg agtgttgagg ctgcggt                                              27

<210> SEQ ID NO 94
<211> LENGTH: 27
<212> TYPE: DNA
<213> ORGANISM: Artificial Sequence
<220> FEATURE:
<223> OTHER INFORMATION: Synthesized

<400> SEQUENCE: 94
gctcagcctg tgtgttcagg caggagg                                              27

<210> SEQ ID NO 95
<211> LENGTH: 27
<212> TYPE: DNA
<213> ORGANISM: Artificial Sequence
<220> FEATURE:
<223> OTHER INFORMATION: Synthesized

<400> SEQUENCE: 95
gctcagcctg agtgttgagg ccccagt                                              27

<210> SEQ ID NO 96
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 96
ggctctccga ggagaaggcc anntrrt                                              27
```

<210> SEQ ID NO 97
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 97
ggctctccga tgggagggcc anngaat                                              27

<210> SEQ ID NO 98
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 98
agctctccga ggagaagagc anngagg                                              27

<210> SEQ ID NO 99
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 99
ggctctctgg ggagaaagcc anngagc                                              27

<210> SEQ ID NO 100
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 100
atctctccga ggaggaggcg anngagt                                              27

<210> SEQ ID NO 101
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 101
ggctctcaga ggagaaggcc gnnggga                                              27

<210> SEQ ID NO 102
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 102
ggctctccga ggagaaggcc anntggt                                27

<210> SEQ ID NO 103
<211> LENGTH: 28
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (23)..(24)
<223> OTHER INFORMATION: n is a, c, g, t or u

<400> SEQUENCE: 103
gcgcccactg caaggcccgg cgnncrrt                               28

<210> SEQ ID NO 104
<211> LENGTH: 28
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (23)..(24)
<223> OTHER INFORMATION: n is a, c, g, t or u

<400> SEQUENCE: 104
gcgcccactg cagggcccgg ctnnggag                               28

<210> SEQ ID NO 105
<211> LENGTH: 28
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (23)..(24)
<223> OTHER INFORMATION: n is a, c, g, t or u

<400> SEQUENCE: 105
gcgcccactg caaggcccgg cgnncggt                               28

<210> SEQ ID NO 106
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 106

```
ggggtcccag gtgctgacgt anntrrt                                          27
```

<210> SEQ ID NO 107
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 107

```
ggggtcccag gtgctgacgt anntagt                                          27
```

<210> SEQ ID NO 108
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, t or u

<400> SEQUENCE: 108

```
gaagtcccag ttgctgacat annggat                                          27
```

<210> SEQ ID NO 109
<211> LENGTH: 27
<212> TYPE: DNA
<213> ORGANISM: Artificial Sequence
<220> FEATURE:
<223> OTHER INFORMATION: Synthesized

<400> SEQUENCE: 109

```
gaaaccacaa acccacaggg agaaatg                                          27
```

<210> SEQ ID NO 110
<211> LENGTH: 29
<212> TYPE: DNA
<213> ORGANISM: Artificial Sequence
<220> FEATURE:
<223> OTHER INFORMATION: Synthesized

<400> SEQUENCE: 110

```
gtactcacct ctcatgaagc acttggggt                                        29
```

<210> SEQ ID NO 111
<211> LENGTH: 29
<212> TYPE: DNA
<213> ORGANISM: Artificial Sequence
<220> FEATURE:
<223> OTHER INFORMATION: Synthesized

<400> SEQUENCE: 111

```
tacctcacct gccaggaagc acttgaaat                                        29
```

<210> SEQ ID NO 112
<211> LENGTH: 27
<212> TYPE: DNA
<213> ORGANISM: Artificial Sequence
<220> FEATURE:
<223> OTHER INFORMATION: Synthesized

<400> SEQUENCE: 112

```
gaaagagaga tgtagggcta gaggggt                                              27

<210> SEQ ID NO 113
<211> LENGTH: 27
<212> TYPE: DNA
<213> ORGANISM: Artificial Sequence
<220> FEATURE:
<223> OTHER INFORMATION: Synthesized

<400> SEQUENCE: 113
gaaagagaga aatagggcta gaacaaa                                              27

<210> SEQ ID NO 114
<211> LENGTH: 27
<212> TYPE: DNA
<213> ORGANISM: Artificial Sequence
<220> FEATURE:
<223> OTHER INFORMATION: Synthesized

<400> SEQUENCE: 114
gaaagaggca tgtagggcta cagaggc                                              27

<210> SEQ ID NO 115
<211> LENGTH: 27
<212> TYPE: DNA
<213> ORGANISM: Artificial Sequence
<220> FEATURE:
<223> OTHER INFORMATION: Synthesized

<400> SEQUENCE: 115
gtaagagaga agtagagcta gaaaaaa                                              27

<210> SEQ ID NO 116
<211> LENGTH: 27
<212> TYPE: DNA
<213> ORGANISM: Artificial Sequence
<220> FEATURE:
<223> OTHER INFORMATION: Synthesized

<400> SEQUENCE: 116
gcaaggcccc aggcatggtg gcacagt                                              27

<210> SEQ ID NO 117
<211> LENGTH: 27
<212> TYPE: DNA
<213> ORGANISM: Artificial Sequence
<220> FEATURE:
<223> OTHER INFORMATION: Synthesized

<400> SEQUENCE: 117
gcagggccag gcccacggag gtacaat                                              27

<210> SEQ ID NO 118
<211> LENGTH: 27
<212> TYPE: DNA
<213> ORGANISM: Artificial Sequence
<220> FEATURE:
<223> OTHER INFORMATION: Synthesized

<400> SEQUENCE: 118
cccaggcctg cagcacagtg gtgcagt                                              27

<210> SEQ ID NO 119
<211> LENGTH: 27
<212> TYPE: DNA
```

```
<213> ORGANISM: Artificial Sequence
<220> FEATURE:
<223> OTHER INFORMATION: Synthesized

<400> SEQUENCE: 119
ctgaggcccg gagcacggag gggagat                                              27

<210> SEQ ID NO 120
<211> LENGTH: 27
<212> TYPE: DNA
<213> ORGANISM: Artificial Sequence
<220> FEATURE:
<223> OTHER INFORMATION: Synthesized

<400> SEQUENCE: 120
gcagggcctg tggcacagag ggcaagg                                              27

<210> SEQ ID NO 121
<211> LENGTH: 27
<212> TYPE: DNA
<213> ORGANISM: Artificial Sequence
<220> FEATURE:
<223> OTHER INFORMATION: Synthesized

<400> SEQUENCE: 121
acagggcccg gcacacggtg tgttggt                                              27

<210> SEQ ID NO 122
<211> LENGTH: 27
<212> TYPE: DNA
<213> ORGANISM: Artificial Sequence
<220> FEATURE:
<223> OTHER INFORMATION: Synthesized

<400> SEQUENCE: 122
ctggggcccg gagcacagtg gggagag                                              27

<210> SEQ ID NO 123
<211> LENGTH: 27
<212> TYPE: DNA
<213> ORGANISM: Artificial Sequence
<220> FEATURE:
<223> OTHER INFORMATION: Synthesized

<400> SEQUENCE: 123
gcagggccct cggcacggtg ggcacca                                              27

<210> SEQ ID NO 124
<211> LENGTH: 27
<212> TYPE: DNA
<213> ORGANISM: Artificial Sequence
<220> FEATURE:
<223> OTHER INFORMATION: Synthesized

<400> SEQUENCE: 124
gtagggcctt cgcgcacctc atggaat                                              27

<210> SEQ ID NO 125
<211> LENGTH: 27
<212> TYPE: DNA
<213> ORGANISM: Artificial Sequence
<220> FEATURE:
<223> OTHER INFORMATION: Synthesized

<400> SEQUENCE: 125
gagtgagtaa gtgtgtgtgt gtgtggt                                              27
```

<210> SEQ ID NO 126
<211> LENGTH: 27
<212> TYPE: DNA
<213> ORGANISM: Artificial Sequence
<220> FEATURE:
<223> OTHER INFORMATION: Synthesized

<400> SEQUENCE: 126
gaatgagtgt gtgtgtgtgt gtgcagt                                27

<210> SEQ ID NO 127
<211> LENGTH: 27
<212> TYPE: DNA
<213> ORGANISM: Artificial Sequence
<220> FEATURE:
<223> OTHER INFORMATION: Synthesized

<400> SEQUENCE: 127
gggagagaga gtgtgtgcgt gtgtggt                                27

<210> SEQ ID NO 128
<211> LENGTH: 27
<212> TYPE: DNA
<213> ORGANISM: Artificial Sequence
<220> FEATURE:
<223> OTHER INFORMATION: Synthesized

<400> SEQUENCE: 128
gaatgagtga gtgtgtgtgt gtgagag                                27

<210> SEQ ID NO 129
<211> LENGTH: 27
<212> TYPE: DNA
<213> ORGANISM: Artificial Sequence
<220> FEATURE:
<223> OTHER INFORMATION: Synthesized

<400> SEQUENCE: 129
gagtgagtga gtgtgtgtgt aagaggt                                27

<210> SEQ ID NO 130
<211> LENGTH: 27
<212> TYPE: DNA
<213> ORGANISM: Artificial Sequence
<220> FEATURE:
<223> OTHER INFORMATION: Synthesized

<400> SEQUENCE: 130
gtgtgagtga gtgtgtgtgt gtgagag                                27

<210> SEQ ID NO 131
<211> LENGTH: 27
<212> TYPE: DNA
<213> ORGANISM: Artificial Sequence
<220> FEATURE:
<223> OTHER INFORMATION: Synthesized

<400> SEQUENCE: 131
gtgtgggtga gtgtgtgcgt gagagcg                                27

<210> SEQ ID NO 132
<211> LENGTH: 27
<212> TYPE: DNA
<213> ORGANISM: Artificial Sequence
<220> FEATURE:

<223> OTHER INFORMATION: Synthesized

<400> SEQUENCE: 132
gaatgagtga gtgtgtgtgt aagaagt    27

<210> SEQ ID NO 133
<211> LENGTH: 27
<212> TYPE: DNA
<213> ORGANISM: Artificial Sequence
<220> FEATURE:
<223> OTHER INFORMATION: Synthesized

<400> SEQUENCE: 133
gagtgagtga gtgtgtatgt gtaagaa    27

<210> SEQ ID NO 134
<211> LENGTH: 27
<212> TYPE: DNA
<213> ORGANISM: Artificial Sequence
<220> FEATURE:
<223> OTHER INFORMATION: Synthesized

<400> SEQUENCE: 134
aggtgagaga gtgtgtgcgt aggagga    27

<210> SEQ ID NO 135
<211> LENGTH: 27
<212> TYPE: DNA
<213> ORGANISM: Artificial Sequence
<220> FEATURE:
<223> OTHER INFORMATION: Synthesized

<400> SEQUENCE: 135
ggctgaatgt gtgtgtgcgt gaatgat    27

<210> SEQ ID NO 136
<211> LENGTH: 27
<212> TYPE: DNA
<213> ORGANISM: Artificial Sequence
<220> FEATURE:
<223> OTHER INFORMATION: Synthesized

<400> SEQUENCE: 136
gactgagtga gtgtgtgagt gagtagt    27

<210> SEQ ID NO 137
<211> LENGTH: 27
<212> TYPE: DNA
<213> ORGANISM: Artificial Sequence
<220> FEATURE:
<223> OTHER INFORMATION: Synthesized

<400> SEQUENCE: 137
gtatgggtga gagtgtgcgt gcacagt    27

<210> SEQ ID NO 138
<211> LENGTH: 27
<212> TYPE: DNA
<213> ORGANISM: Artificial Sequence
<220> FEATURE:
<223> OTHER INFORMATION: Synthesized

<400> SEQUENCE: 138
gtgtgaatga gtgtgtgtgt gagtgga    27

```
<210> SEQ ID NO 139
<211> LENGTH: 27
<212> TYPE: DNA
<213> ORGANISM: Artificial Sequence
<220> FEATURE:
<223> OTHER INFORMATION: Synthesized

<400> SEQUENCE: 139
gggtgagtga gtgagtgagt gagtgag                                       27

<210> SEQ ID NO 140
<211> LENGTH: 27
<212> TYPE: DNA
<213> ORGANISM: Artificial Sequence
<220> FEATURE:
<223> OTHER INFORMATION: Synthesized

<400> SEQUENCE: 140
aagtgagtga gtgtgtgtgt gcaaaac                                       27

<210> SEQ ID NO 141
<211> LENGTH: 27
<212> TYPE: DNA
<213> ORGANISM: Artificial Sequence
<220> FEATURE:
<223> OTHER INFORMATION: Synthesized

<400> SEQUENCE: 141
gagtgagtga gtgtgtgtgt gtgagag                                       27

<210> SEQ ID NO 142
<211> LENGTH: 27
<212> TYPE: DNA
<213> ORGANISM: Artificial Sequence
<220> FEATURE:
<223> OTHER INFORMATION: Synthesized

<400> SEQUENCE: 142
aggtgtgtga gtgtgtgtgt gtgaaac                                       27

<210> SEQ ID NO 143
<211> LENGTH: 27
<212> TYPE: DNA
<213> ORGANISM: Artificial Sequence
<220> FEATURE:
<223> OTHER INFORMATION: Synthesized

<400> SEQUENCE: 143
gggtgggtga gtgagtgagt gaggagt                                       27

<210> SEQ ID NO 144
<211> LENGTH: 27
<212> TYPE: DNA
<213> ORGANISM: Artificial Sequence
<220> FEATURE:
<223> OTHER INFORMATION: Synthesized

<400> SEQUENCE: 144
gagtgagtga gtgtgtgtgt gtaaaaa                                       27

<210> SEQ ID NO 145
<211> LENGTH: 27
<212> TYPE: DNA
<213> ORGANISM: Artificial Sequence
<220> FEATURE:
<223> OTHER INFORMATION: Synthesized
```

<400> SEQUENCE: 145
gagtgagtga gtgagtgagt gaaaggt                    27

<210> SEQ ID NO 146
<211> LENGTH: 27
<212> TYPE: DNA
<213> ORGANISM: Artificial Sequence
<220> FEATURE:
<223> OTHER INFORMATION: Synthesized

<400> SEQUENCE: 146
ggatgagtgt gtgtgtgcgt gtaacaa                    27

<210> SEQ ID NO 147
<211> LENGTH: 28
<212> TYPE: DNA
<213> ORGANISM: Artificial Sequence
<220> FEATURE:
<223> OTHER INFORMATION: Synthesized

<400> SEQUENCE: 147
gtgtggttcc agaaccggcg gatgaagt                   28

<210> SEQ ID NO 148
<211> LENGTH: 28
<212> TYPE: DNA
<213> ORGANISM: Artificial Sequence
<220> FEATURE:
<223> OTHER INFORMATION: Synthesized

<400> SEQUENCE: 148
atctggttcc agaaccgcag gatgaagt                   28

<210> SEQ ID NO 149
<211> LENGTH: 28
<212> TYPE: DNA
<213> ORGANISM: Artificial Sequence
<220> FEATURE:
<223> OTHER INFORMATION: Synthesized

<400> SEQUENCE: 149
gtatggtttc agaaccgaag aacaaagt                   28

<210> SEQ ID NO 150
<211> LENGTH: 28
<212> TYPE: DNA
<213> ORGANISM: Artificial Sequence
<220> FEATURE:
<223> OTHER INFORMATION: Synthesized

<400> SEQUENCE: 150
ttatggttcc agaaacgaag gaagcaat                   28

<210> SEQ ID NO 151
<211> LENGTH: 28
<212> TYPE: DNA
<213> ORGANISM: Artificial Sequence
<220> FEATURE:
<223> OTHER INFORMATION: Synthesized

<400> SEQUENCE: 151
gtgtggttcc agaaccgcag gaccaagt                   28

<210> SEQ ID NO 152
<211> LENGTH: 28

```
<212> TYPE: DNA
<213> ORGANISM: Artificial Sequence
<220> FEATURE:
<223> OTHER INFORMATION: Synthesized

<400> SEQUENCE: 152
acctggttcc agaaccagag gatgaaat                                              28

<210> SEQ ID NO 153
<211> LENGTH: 28
<212> TYPE: DNA
<213> ORGANISM: Artificial Sequence
<220> FEATURE:
<223> OTHER INFORMATION: Synthesized

<400> SEQUENCE: 153
gtctggttcc agaaccgaag ggccaagt                                              28

<210> SEQ ID NO 154
<211> LENGTH: 28
<212> TYPE: DNA
<213> ORGANISM: Artificial Sequence
<220> FEATURE:
<223> OTHER INFORMATION: Synthesized

<400> SEQUENCE: 154
atctggtttc agaaccggag gatgaagt                                              28

<210> SEQ ID NO 155
<211> LENGTH: 28
<212> TYPE: DNA
<213> ORGANISM: Artificial Sequence
<220> FEATURE:
<223> OTHER INFORMATION: Synthesized

<400> SEQUENCE: 155
ccaaggtccc ggaaccgaag gaggaagg                                              28

<210> SEQ ID NO 156
<211> LENGTH: 28
<212> TYPE: DNA
<213> ORGANISM: Artificial Sequence
<220> FEATURE:
<223> OTHER INFORMATION: Synthesized

<400> SEQUENCE: 156
atttggttcc agaaccggcg gatgaaat                                              28

<210> SEQ ID NO 157
<211> LENGTH: 28
<212> TYPE: DNA
<213> ORGANISM: Artificial Sequence
<220> FEATURE:
<223> OTHER INFORMATION: Synthesized

<400> SEQUENCE: 157
atctggttcc agaaccgcag gatgaaaa                                              28

<210> SEQ ID NO 158
<211> LENGTH: 28
<212> TYPE: DNA
<213> ORGANISM: Artificial Sequence
<220> FEATURE:
<223> OTHER INFORMATION: Synthesized

<400> SEQUENCE: 158
```
acgtggttcc agaaccggcg gatgaagc                                    28

<210> SEQ ID NO 159
<211> LENGTH: 28
<212> TYPE: DNA
<213> ORGANISM: Artificial Sequence
<220> FEATURE:
<223> OTHER INFORMATION: Synthesized

<400> SEQUENCE: 159
acgtggtacc agaatcggag gatgaagt                                    28

<210> SEQ ID NO 160
<211> LENGTH: 27
<212> TYPE: DNA
<213> ORGANISM: Artificial Sequence
<220> FEATURE:
<223> OTHER INFORMATION: Synthesized

<400> SEQUENCE: 160
acacagccag agggttgagg cggaggt                                     27

<210> SEQ ID NO 161
<211> LENGTH: 27
<212> TYPE: DNA
<213> ORGANISM: Artificial Sequence
<220> FEATURE:
<223> OTHER INFORMATION: Synthesized

<400> SEQUENCE: 161
gttcagccca agtgttgaga ctcaggt                                     27

<210> SEQ ID NO 162
<211> LENGTH: 27
<212> TYPE: DNA
<213> ORGANISM: Artificial Sequence
<220> FEATURE:
<223> OTHER INFORMATION: Synthesized

<400> SEQUENCE: 162
actgagcctg agggttgagg ctgcagt                                     27

<210> SEQ ID NO 163
<211> LENGTH: 27
<212> TYPE: DNA
<213> ORGANISM: Artificial Sequence
<220> FEATURE:
<223> OTHER INFORMATION: Synthesized

<400> SEQUENCE: 163
gcccagccag gatgttgagg ctgcaat                                     27

<210> SEQ ID NO 164
<211> LENGTH: 27
<212> TYPE: DNA
<213> ORGANISM: Artificial Sequence
<220> FEATURE:
<223> OTHER INFORMATION: Synthesized

<400> SEQUENCE: 164
ggctctccga ggagaaggcc aagtggt                                     27

<210> SEQ ID NO 165
<211> LENGTH: 27
<212> TYPE: DNA
<213> ORGANISM: Artificial Sequence

```
<220> FEATURE:
<223> OTHER INFORMATION: Synthesized

<400> SEQUENCE: 165
ggctctccga tgggagggcc agagaat                                              27

<210> SEQ ID NO 166
<211> LENGTH: 27
<212> TYPE: DNA
<213> ORGANISM: Artificial Sequence
<220> FEATURE:
<223> OTHER INFORMATION: Synthesized

<400> SEQUENCE: 166
agctctccga ggagaagagc agcaagg                                              27

<210> SEQ ID NO 167
<211> LENGTH: 27
<212> TYPE: DNA
<213> ORGANISM: Artificial Sequence
<220> FEATURE:
<223> OTHER INFORMATION: Synthesized

<400> SEQUENCE: 167
ggctctctgg ggagaaagcc agggagc                                              27

<210> SEQ ID NO 168
<211> LENGTH: 27
<212> TYPE: DNA
<213> ORGANISM: Artificial Sequence
<220> FEATURE:
<223> OTHER INFORMATION: Synthesized

<400> SEQUENCE: 168
aactctccca ggagaaggcc cagaaat                                              27

<210> SEQ ID NO 169
<211> LENGTH: 27
<212> TYPE: DNA
<213> ORGANISM: Artificial Sequence
<220> FEATURE:
<223> OTHER INFORMATION: Synthesized

<400> SEQUENCE: 169
gcctctccaa ggagaagggg ccagaag                                              27

<210> SEQ ID NO 170
<211> LENGTH: 27
<212> TYPE: DNA
<213> ORGANISM: Artificial Sequence
<220> FEATURE:
<223> OTHER INFORMATION: Synthesized

<400> SEQUENCE: 170
ggctctctgg ggagaaggga caaggag                                              27

<210> SEQ ID NO 171
<211> LENGTH: 27
<212> TYPE: DNA
<213> ORGANISM: Artificial Sequence
<220> FEATURE:
<223> OTHER INFORMATION: Synthesized

<400> SEQUENCE: 171
atctctccga ggaggaggcg aaggagt                                              27
```

<210> SEQ ID NO 172
<211> LENGTH: 27
<212> TYPE: DNA
<213> ORGANISM: Artificial Sequence
<220> FEATURE:
<223> OTHER INFORMATION: Synthesized

<400> SEQUENCE: 172
ggctctcaga ggagaaggcc gagggga                                27

<210> SEQ ID NO 173
<211> LENGTH: 28
<212> TYPE: DNA
<213> ORGANISM: Artificial Sequence
<220> FEATURE:
<223> OTHER INFORMATION: Synthesized

<400> SEQUENCE: 173
gtctctccca ggagactggc caaagagg                               28

<210> SEQ ID NO 174
<211> LENGTH: 27
<212> TYPE: DNA
<213> ORGANISM: Artificial Sequence
<220> FEATURE:
<223> OTHER INFORMATION: Synthesized

<400> SEQUENCE: 174
agctctccaa ggagaagcca aaaaatc                                27

<210> SEQ ID NO 175
<211> LENGTH: 27
<212> TYPE: DNA
<213> ORGANISM: Artificial Sequence
<220> FEATURE:
<223> OTHER INFORMATION: Synthesized

<400> SEQUENCE: 175 ggctcccca ggagatgacc agatagt                                 27

<210> SEQ ID NO 176
<211> LENGTH: 27
<212> TYPE: DNA
<213> ORGANISM: Artificial Sequence
<220> FEATURE:
<223> OTHER INFORMATION: Synthesized

<400> SEQUENCE: 176
agttctccaa ggagaagacc acgtggt                                27

<210> SEQ ID NO 177
<211> LENGTH: 28
<212> TYPE: DNA
<213> ORGANISM: Artificial Sequence
<220> FEATURE:
<223> OTHER INFORMATION: Synthesized

<400> SEQUENCE: 177
gcgcccactg caaggcccgg cgcacggt                               28

<210> SEQ ID NO 178
<211> LENGTH: 28
<212> TYPE: DNA
<213> ORGANISM: Artificial Sequence
<220> FEATURE:
<223> OTHER INFORMATION: Synthesized

```
<400> SEQUENCE: 178
aggcccactg caaggcccag tgggcggc                                          28

<210> SEQ ID NO 179
<211> LENGTH: 28
<212> TYPE: DNA
<213> ORGANISM: Artificial Sequence
<220> FEATURE:
<223> OTHER INFORMATION: Synthesized

<400> SEQUENCE: 179
gcgcccactg cagggcccgg ctgcggag                                          28

<210> SEQ ID NO 180
<211> LENGTH: 27
<212> TYPE: DNA
<213> ORGANISM: Artificial Sequence
<220> FEATURE:
<223> OTHER INFORMATION: Synthesized

<400> SEQUENCE: 180
ggggtcccag gtgctgacgt aggtagt                                           27
```

MODIFIED PROTEIN AND METHOD FOR ALTERING GENOME OF CELL

SEQUENCE LISTING

The Sequence Listing file entitled "mkcp406sequencelisting" having a size of 72,282 bytes and a creation date of Dec. 4, 2020, is incorporated herein by reference in its entirety.

TECHNICAL FIELD

The present invention relates to a modified protein and its use in altering the genome of a cell. Particularly, but not exclusively, the invention relates to a modified *Streptococcus aureus* Cas9 (SaCas9) protein and its use in genomic engineering, genome targeting and genome editing technologies.

BACKGROUND OF THE INVENTION

Genome engineering technologies have enabled systematic interrogation of genome function and hold great potential for gene therapy. The clustered regularly interspaced short palindromic repeat (CRISPR) associated protein (Cas) system enables efficient DNA modification guided by a complementary RNA and in the presence of a protospacer adjacent motif (PAM). However, non-perfect guide-RNA-target-DNA matching has been known to occur which can result in modifications at genomic loci other than the intended locus. This off-target activity can limit the broad application of this technology. Accordingly, modified proteins for altering the genome of a cell with application in genome editing and gene therapy are desired.

SUMMARY OF THE INVENTION

In a first aspect, the invention provides a modified protein. Preferably, the modified protein is a *Streptococcus aureus* Cas9 (SaCas9) protein with a mutation at an N413 position, and optionally one or more of a nuclear localization sequence, a cell penetrating peptide sequence, an affinity tag and/or a fusion base editor protein.

In an embodiment, the modified protein comprises an amino acid sequence as defined in SEQ ID NO: 1 or a homologue thereof.

In an embodiment, the modified protein comprises an amino acid sequence as defined in SEQ ID NO: 2 or a homologue thereof.

In an embodiment, the modified protein further comprises one or more mutations at R245, N419 and/or R654 positions.

In an embodiment, the modified protein comprises an amino acid sequence as defined in SEQ ID NO: 3 or a homologue thereof.

In an embodiment, the modified protein comprises an amino acid sequence as defined in SEQ ID NO: 4 or a homologue thereof.

In an embodiment, the modified protein with optionally at least one additional mutation selected from the group consisting of R245, N419 and R654 positions decreases nuclease activity at one or more sites on a target DNA molecule.

In an embodiment, the one or more sites are off-target sites on the target DNA molecule.

In an embodiment, the mutation is a single amino acid substitution.

In an embodiment, the modified protein comprises alanine at the N413 position. In an embodiment, the modified protein comprises alanine at the N413, R245, N419 and/or R654 position.

In a second aspect, the invention pertains to a method for altering a genome of a cell. The method comprises the step of using the modified protein.

In an embodiment, the modified protein is expressed in the cell, or the cell is contacted with the modified protein and a guide RNA having a region complementary to a selected portion of the genome of the cell.

In a third aspect, the invention pertains to a kit comprising the modified protein. In an embodiment, the kit comprises a modified *Streptococcus aureus* Cas9 (SaCas9) protein with a mutation at an N413 position, and optionally one or more of a nuclear localization sequence, a cell penetrating peptide sequence, an affinity tag and/or a fusion base editor protein.

In an embodiment, the modified protein comprises an amino acid sequence as defined in SEQ ID NO: 1 or a homologue thereof. In a further embodiment, the modified protein comprises an amino acid sequence as defined in SEQ ID NO: 2 or a homologue thereof.

In an embodiment, the modified protein comprising a sequence as defined in SEQ ID NO: 1 or SEQ ID NO: 2 or a homologue thereof further comprises one or more mutations at R245, N419 and/or R654 positions.

In an embodiment, the modified protein further comprises mutations at R245, N419 and R654 positions, preferably the modified protein comprises an amino acid sequence as defined in SEQ ID NO: 3 or a homologue thereof.

In an embodiment, the modified protein further comprises mutations at R245, N419 and R654 positions, preferably the modified protein comprises an amino acid sequence as defined in SEQ ID NO: 4 or a homologue thereof.

In an embodiment, the mutation is a single amino acid substitution.

In an embodiment, the modified protein comprises alanine at the N413 position. In a further embodiment, the modified protein comprises alanine at the N413, R245, N419 and/or R654 positions.

Accordingly, the invention provides a novel and effective modified protein for altering the genome of a cell with application in genome editing and gene therapy. The modified protein of the invention, specifically the modified *Streptococcus aureus* Cas9 (SaCas9) protein with a mutation at an N413 position, confers high genome-wide specificity and retains high editing efficiency. The provision of the modified SaCas9 protein of the present invention and a guide RNA (gRNA) establishes a gene-editing system in a cell. The Cas9 protein is guided by the gRNA to cut a target gene at a specific location on a target DNA molecule of a cell. The application of the modified SaCas9 protein of the invention advantageously decreases nuclease activity at one or more off-target positions on a target DNA molecule thereby enabling genome-editing applications with high genome-wide precision. This results in significant reductions of off-target activity and improved specificity of the SaCas9 protein. The modified protein and the related kit comprising it are also parts of the invention.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

FIG. 1C is a diagram showing the structural domains of SaCas9 and the positions of four amino acid residues, R245, N413, N419 and R654.

FIG. 1D is a bar graph showing the percentage of insertions or deletions of bases (indels) on human endogenous site EMX1_6 in HEK293T cells using wild-type SaCas9 (WT), single amino acid substitution SaCas9 modified proteins R245A, N413A, N419A and R654A, and a no-Cas9 negative control (NC).

FIG. 1E is a bar graph showing the percentage of indels on human endogenous site VEGFA_8 in HEK293T cells using wild-type SaCas9 (WT), single amino acid substitution SaCas9 modified proteins R245A, N413A, N419A and R654A, and a no-Cas9 negative control (NC).

FIG. 1F is a bar graph showing the percentage of indels on human endogenous site EMX1_1 in HEK293T cells using wild-type SaCas9 (WT), single amino acid substitution SaCas9 modified proteins R245A, N413A, N419A and R654A, and a no-Cas9 negative control (NC).

FIG. 3B shows genome-wide cleavage sites detected by GUIDE-seq on FANCF_13. Read counts listed on the right represent the number of GUIDE-Seq reads; on-target site is indicated by "*" and mismatched bases in off-target sites with the on-target site are highlighted.

FIG. 3F shows genome-wide cleavage sites detected by GUIDE-Seq at canonical NNGRRT PAM sites.

DETAILED DESCRIPTION OF THE EMBODIMENTS

Figure 1A:
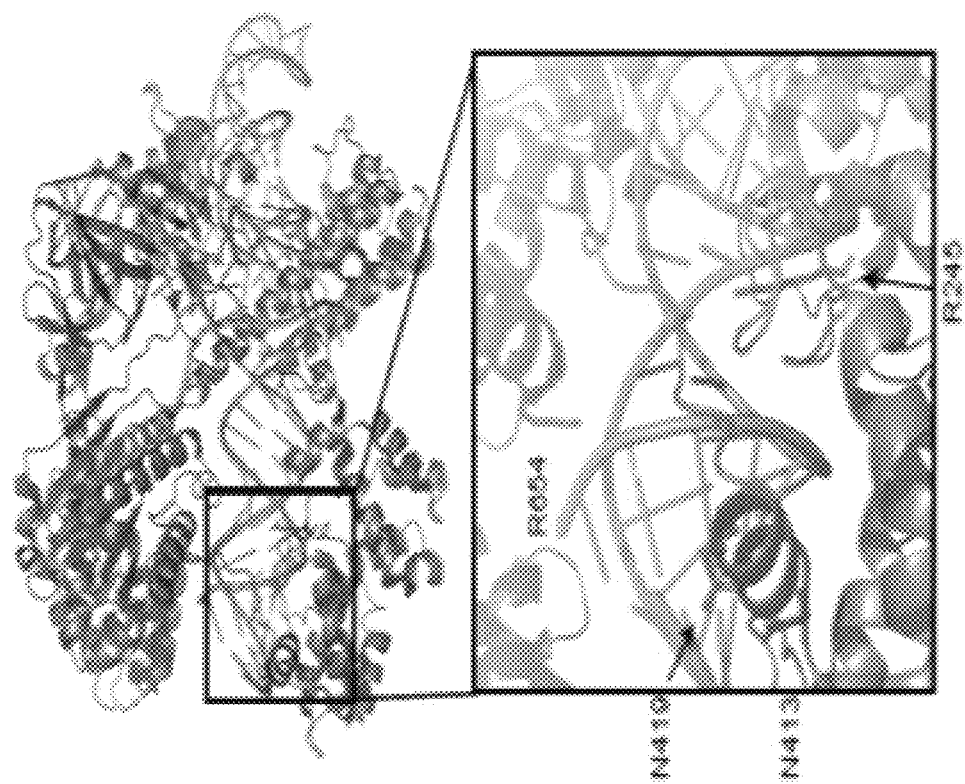
FIG. 1A is a figure of a crystal structure of wild-type *Streptococcus aureus* Cas9 (SaCas9) interacting with a guide RNA (gRNA)-target DNA heteroduplex. A magnified structure of the active site shows the amino acid residues at the R245, N413, N419 and R654 (in red) positions (also known as amino acid residues R245, N413, N419 and R654) that form polar contacts within 3.0 Å distance from the target DNA (in green).

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise.

The present invention relates to a modified protein and its use in altering the genome of a cell. Particularly, the invention relates to a modified *Streptococcus aureus* Cas9 (SaCas9) protein and its use in genomic engineering, genome targeting and genome editing technologies. For example, one of the applications of the modified proteins is as RNA-guided clustered, regularly interspaced, short palindromic repeats (CRISPR)-Cas9 proteins, for example a SaCas9 modified protein. A limitation of CRISPR-SaCas9 proteins that restricts broad application are their activities on off-target sites with the potential to induce undesired off-target mutations and disrupt the functionality of otherwise normal genes.

The provision of the modified SaCas9 protein of the present invention and a guide RNA (gRNA) establishes a gene-editing system in a cell. CRISPR-SaCas9 proteins, guided by the gRNA, bind and cleave a predetermined target sequence of a target gene at a specific location, i.e. an on-target site, on a target DNA molecule, thereby resulting in a double stranded chromosomal break at the on-target site that leads to site-specific modifications by the cell. The "target gene" as used herein refers to a gene of interest. The Cas9 protein recognizes a short DNA sequence, the protospacer adjustment motif (PAM), found downstream of the target sequence, usually three to four nucleotides downstream from the cut site. The PAM sequence is an essential component of the CRISPR-Cas9 system and the Cas9 protein will not bind to or cleave the target DNA sequence without the downstream PAM sequence. The SaCas9 protein, for example, recognizes the canonical PAM sequence NNGRRT or the non-canonical PAM sequence NNNRRT.

Non-specific binding at locations other than the target sequence, i.e. at off-target sites, of the CRISPR-Cas9 has been known to occur, thus resulting in cleaving of off-target sequences and causing non-specific genetic modifications. The inventors have found that the number of mismatched bases in the guide RNA-target DNA heteroduplex at a PAM-distal region (for example, positions 10 to 20 from the PAM) may be inversely correlated with the proportion of SaCas9 in an activated state and that wild-type SaCas9 amino acid residues in proximity of the guide RNA-target DNA heteroduplex could lower the threshold for activating the Cas9 nuclease domain, thus resulting in potentially more binding at off-target sites.

The modified protein as described herein advantageously provides an improved Cas9 protein with reduced nuclease activity at one or more sites on a target DNA molecule, specifically at one or more off-target sites on a target DNA molecule, such that off-target activities and undesired off-target mutations on the target DNA molecule are reduced. The term "off-target sites" as used herein refers to non-specific binding of the modified protein at locations other than the predetermined target sequence. The term "on-target sites" used herein refers to binding of the modified protein at the predetermined target sequence. On-target and off-target site binding may be compared at various target sites, for example human endogenous sites. The target sites include, but are not limited to, EMX1_6, EMX1_1, EMX1_4, EMX1_10, VEGFA_8, FANCF_13, FANCF_10, FANCF_9, FANCF_16, RUNX1_13, and RUNX1_14.

The present invention in the first aspect provides a modified Cas9 protein with a mutation at an N413 position, i.e. a mutation of the amino acid at N413, and optionally one or more of a nuclear localization sequence, a cell penetrating peptide sequence, an affinity tag and/or a fusion base editor protein. Preferably, the modified protein is a *Streptococcus aureus* Cas9 protein. A mutation of an amino acid alters the amino acid to an amino acid other than the wild-type amino acid. Alternatively, a mutation may be resulted from a deletion of an amino acid residue in the amino acid sequence or an addition of one or more amino acid residues into the amino acid sequence, thereby altering the binding activity between the amino acid sequence and the target sequence. In an example embodiment, the mutation is a single amino acid substitution whereby the wild-type amino acid is changed to any amino acid other than the wild-type amino acid. In a preferred embodiment, the mutation changes the wild-type amino acid to alanine.

In an example embodiment, the modified Cas9 protein includes an amino acid sequence as defined in SEQ ID NO: 1 or a homologue thereof wherein the modified protein comprising the amino acid sequence includes a mutation at an N413 position. In a preferred embodiment, the modified protein comprising or consisting of the amino acid sequence includes an alanine at the N413 position.

In another example embodiment, the modified protein includes an amino acid sequence as defined in SEQ ID NO: 2 or a homologue thereof wherein the modified protein comprising or consisting of the amino acid sequence includes three E782K, N968K, R1015H substitutions and a mutation at an N413 position. In a preferred embodiment, the modified protein comprising or consisting of the amino acid sequence includes an alanine at the N413 position.

In some embodiments, the modified protein includes one, two, or three mutations at the R245, N419 or R654 positions in addition to a mutation at the N413 position. For example, the modified protein may include one or more mutations at R245 and/or N419 and a further mutation at R654. In a preferred embodiment, the modified protein comprises an amino acid sequence as defined in SEQ ID NO: 3 or a homologue thereof and includes a mutation at N413, N419, R245 and R654 positions, also referred to as SaCas9-HF. In an embodiment, the mutation at one or more of the N413, N419, R245 and/or R654 positions is a single amino acid substitution. In a preferred embodiment, the modified protein comprising or consisting of the amino acid sequence includes an alanine at the N413, N419, R245 and/or R654 positions.

In an embodiment, the modified protein includes one, two, or all three of the following mutations at the R245, N419 or R654 positions and three E782K,N968K and R1015H mutations and a mutation at an N413 position. In a particular embodiment, the modified protein comprises an amino acid sequence as defined in SEQ ID NO: 4 of a homologue thereof wherein the modified protein includes mutations at the N413, N419, R245 and R654 positions and three E782K,N968K,R1015H mutations, also referred to as KKH-SaCas9-HF. In an embodiment, the mutation at one or more of the N413, N419, R245 and/or R654 positions is a single amino acid substitution. Preferably, the modified protein comprising or consisting of the amino acid sequence includes an alanine at the N413, N419, R245 and/or R654 positions.

The term "homologue" used herein refers to amino acids having a sequence identity of at least 50%, at least 60%, at least 70%, at least 80%, at least 90% or at least 95% to the modified protein according to the present invention. In an embodiment, the homologue of the modified protein has at least 90%, 91%, 92%, 93%, 94%, 95%, 96%, 97%, 98%, or 99% overall sequence identity to the modified protein. In a particular embodiment, the modified protein consists of a sequence of SEQ ID NO: 1, SEQ ID NO: 2, SEQ ID NO: 3, SEQ ID NO: 4 or a homologue thereof.

The term 'cell penetrating peptides' used herein refers to peptides that facilitate the movement of a wide range of biomolecules across the cell membrane into the cytoplasm or an organelle. Examples of biomolecules that cell penetrating peptides can deliver include, but are not limited to, plasmid DNA, oligonucleotides, nanoparticles, peptide-nucleic acid (PNA), siRNA, proteins, peptides and/or liposomes. Examples of cell penetrating peptides commonly used in the art include trans-activating transcriptional activator (TAT), penetratin, etc. The modified protein of the present invention can include a cell penetrating peptide sequence.

The term 'nuclear localization sequence' used herein refers to amino acid sequence that facilitates the transport of proteins into the nucleus of a cell. Examples known in the art include SV40 large T antigen NLS and nucleoplasmin NLS. The modified protein of the present invention can include, alternatively or in addition to the cell penetrating peptide sequence, a nuclear localization sequence.

The term 'affinity tag' as used herein facilitates the purification of recombinant modified proteins, for example GST, FLAG or hexahistidine sequences. The term 'fusion base editor protein' as used herein refers to proteins that enable the direct conversion or editing of bases.

In a preferred embodiment, the modified protein with a mutation at the N413 position and at least one additional mutation at the R245, N419 and/or R654 positions decrease nuclease activity at one or more sites on a target DNA molecule. In a preferred embodiment, the sites are off-target sites. Preferably, the mutation changes the wild-type amino acid to alanine.

The modified SaCas9 protein of the present invention is derived from an isolated SaCas9 protein. The isolated SaCas9 protein may be commercially available or artificially synthesized. The isolated SaCas9 protein is then subject to amino acid modification particularly at the N413 position, under suitable conditions, to produce the modified SaCas9 protein as described above. The modified SaCas9 protein may be provided in a kit which is suitable for altering the genome of a cell or a subject. Accordingly, the present invention also pertains to a kit comprising the modified protein as described above.

In an embodiment, the kit includes a modified Cas9 protein with a mutation at an N413 position, and optionally one or more of a nuclear localization sequence, a cell penetrating peptide sequence, an affinity tag and/or a fusion base editor protein. In one embodiment, the modified protein includes an amino acid sequence as defined in SEQ ID NO: 1 or a homologue thereof wherein the modified protein comprising the amino acid sequence includes a mutation at an N413 position.

In a further embodiment, the modified protein with a mutation at an N413 position further includes one or more mutations at the R245, N419 or R654 positions. In a particular embodiment, the modified protein comprises an amino acid sequence as defined in SEQ ID NO: 3 or a homologue thereof that includes a mutation at N413, N419, R245 and R654 positions. In a preferred embodiment, the mutation is a single amino acid substitution. In another preferred embodiment, the modified protein includes an alanine at the N413 position, and/or optionally at the N419, R245 and R654 positions.

In some embodiments, the modified protein with a mutation at an N413 position further includes three E782K, N968K and R1015H mutations. In a particular embodiment, the modified protein includes an amino acid sequence as defined in SEQ ID NO: 2 or a homologue thereof.

In an embodiment, the modified protein comprising a mutation at an N413 position and three mutations E782K, N968K and R1015H further includes one or more mutations at the R245, N419 and/or R654 positions. In a particular embodiment, the modified protein comprises an amino acid sequence as defined in SEQ ID NO: 4 or a homologue thereof that includes a mutation at N413, N419, R245 and R654 positions and three mutations E782K, N968K and R1015H. In a preferred embodiment, the mutation at the N413, N419, R245 and/or R654 positions is a single amino acid substitution. In another preferred embodiment, the modified protein includes an alanine at the N413 position, and/or optionally at the N419, R245 and R654 positions.

Preferably, the kit further comprises gRNA that guides the modified Cas9 protein of the invention to cut a target gene at a specific location on a target DNA molecule of a cell. The gRNA may be ligated into a vector, such as a commercially available vector or a vector prepared and synthesized in a laboratory. A person skilled in the art would appreciate the appropriate vector for carrying the gRNA molecule of the invention, and the conditions for inserting the gRNA molecule into the vector. The presence of the gRNA and the modified Cas9 protein provides suitable conditions for altering the target gene in that particular cell.

Preferably, the kit further comprises an inducible promoter. The term "inducible promoter" as used herein refers to a chemical or molecule that can control gene expression of a particular gene, in particular inducing a target gene to express in a system. The inducible promoter may include a tetracycline including tetracycline-type antibiotic or its derivative which is capable of inducing the expression of a target gene.

It would be appreciated that the kit may further comprise other suitable excipients such as buffers or reagents for facilitating the application of the kit. Preferably, the kit may be applied in various applications such as medical applications including therapies and diagnosis, researches and the like. Accordingly, the modified SaCas9 protein and the kit of the present invention may be used in the preparation of a medicament for treatment and/or in the preparation of an agent for research study.

The present invention further pertains to a CRIPSR system comprising a modified SaCas9 protein as described above or a gene encoding said SaCas9 protein, a gRNA as described above, and optionally an inducible promoter. In an embodiment, the gene encoding the modified SaCas9 protein may be provided in a recombinant vector.

The term "recombinant vector" as used herein refers to a vector such as a plasmid that contains a foreign nucleic acid introduced therein. The recombinant vector is then inserted into a cell for example through infection. The transcription of the recombinant vector allows the transcription of the foreign nucleic acid and thus may result in expression of the foreign nucleic acid. A person skilled in the art would appreciate suitable methods for introducing the recombinant vector into a cell for infection.

In a further aspect, the invention provides a method for altering the genome of a cell, the method including the step of using a modified SaCas9 protein of the invention with a mutation at an N413 position, and optionally one or more of a nuclear localization sequence, a cell penetrating peptide sequence, an affinity tag and/or a fusion base editor protein. The method of altering the genome of the cell may include, for example, contacting the cell with, or expressing in the cell, the modified SaCas9 protein as described above, and a gRNA having a region complementary to a selected portion of the genome of the cell with optimal nucleotide spacing at the genomic target site.

In one embodiment, the modified protein includes an amino acid sequence as defined in SEQ ID NO: 1 or a homologue thereof wherein the modified protein comprising the amino acid sequence includes a mutation at an N413 position.

In a further embodiment, the modified protein including a mutation at an N413 position further includes one or more mutations at the R245, N419 or R654 positions. In a particular embodiment, the modified protein comprises an amino acid sequence as defined in SEQ ID NO: 3 or a homologue thereof that includes a mutation at N413, N419, R245 and R654 positions. In a preferred embodiment, the mutation is a single amino acid substitution. In a most preferred embodiment, the modified protein includes an alanine at the N413 position, and/or optionally at the N419, R245 and R654 positions.

In some embodiments, the modified protein includes an amino acid sequence as defined in SEQ ID NO: 2 or a homologue thereof wherein the modified protein comprising the amino acid sequence includes three E782K, N968K, R1015H mutations and a mutation at an N413 position.

In an embodiment, the modified protein comprising mutations at E782, N968, R1015 and N413 positions further includes one or more mutations at the R245, N419 and/or R654 positions. In a particular embodiment, the modified protein comprises an amino acid sequence as defined in SEQ ID NO: 4 or a homologue thereof that includes a mutation at N413, N419, R245, R654, E782, N968 and R1015 positions. In a preferred embodiment, the mutation is a single amino acid substitution. In a most preferred embodiment, the modified protein includes an alanine at the N413 position, and/or optionally at the N419, R245 and R654 positions.

Accordingly, the invention provides a novel and effective approach for altering the genome of a cell, for example by contacting a cell with, or expressing in the cell, a modified SaCas9 protein with a mutation at an N413 position, and optionally one or more of a nuclear localization sequence, a cell penetrating peptide sequence, an affinity tag and/or a fusion base editor protein. The inventors unexpectedly found that modification of the amino acid residues at the N413 position and optionally one or more mutations at the R245, N419 and/or R654 positions decreased nuclease activity at one or more off-target sites on a target DNA molecule, such that non-specific binding and off-target cleavages were reduced without compromising on-target binding. The modified SaCas9 protein of the invention has advantageously enhanced targeting specificity and thus broader application.

The invention is now described in the following non-limiting examples.

EXAMPLES

The mutant proteins were generated by the site-specific mutagenesis approach using overlapping PCR primers that contain desired mutant bases to amplify the wild-type protein encoding DNA sequence, and cloned into expression vector. To compare the effect of wild-type and mutant proteins in nuclease activity, the GUIDE-seq (genome-wide unbiased identification of double-stranded breaks enabled by sequencing) was used. Briefly, double-stranded oligo deoxyribonucleotides (dsODNs) were co-delivered with Cas9 and target guide (sgRNA)-expressing plasmid(s) into target cells. Following the Cas9 gene editing that introduced double strand breaks in on- and off-targets of the genome, the dsODNs were randomly integrated into the breaks (DSBs). DNA was extracted from the cells, and sequencing libraries were prepared by enriching the dsODNs and their flanking sequences and used for next-generation sequencing. The resulting number of reads is proportional to the DSB events occurred during the experiment, and the read sequences were aligned to a reference genome to identify DSBs introduced by Cas9.

Example 1

Structure-Guided Protein Engineering for High-Fidelity SaCas9

Figure 1B:
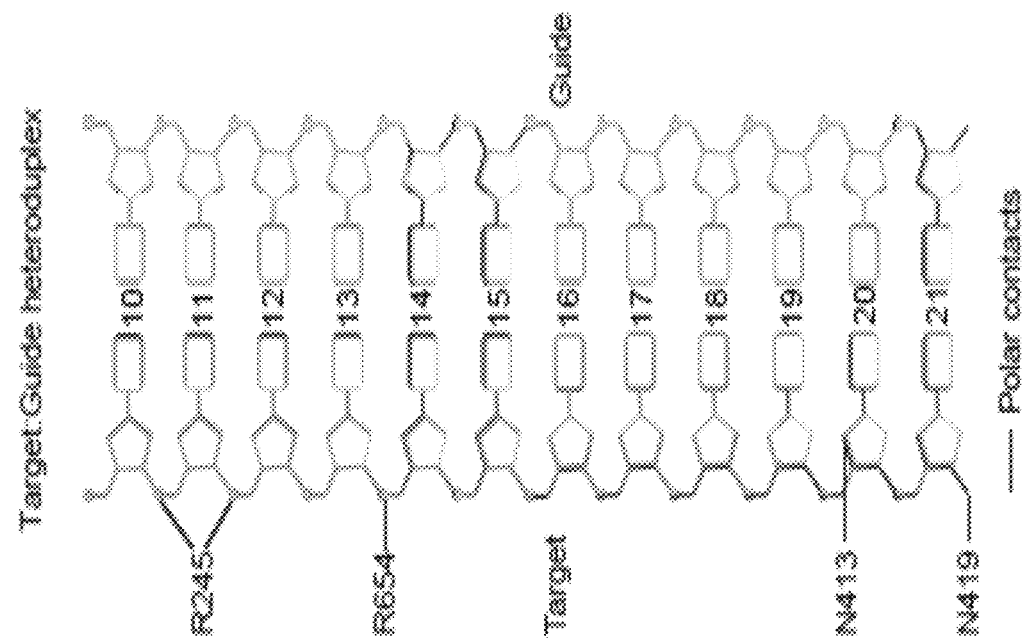
FIG. 1B is a diagram showing SaCas9 amino acid residues in contact with the gRNA-target DNA heteroduplex labeled with protospacer positions, with 21 being most proximal to the protospacer adjacent motif (PAM) on the target DNA.

With reference to FIG. 1A, the inventors identified, by generating crystal structure data of the SaCas9/sgRNA-target-DNA complex, four amino acid residues, specifically R245, N413, N419, and R654 form polar contacts within 3.0 Å distance from the DNA target (as illustrated in FIG. 1B). As shown in FIG. 1C, three of these amino acid residues, specifically R245, N413 and N419, are located in the recognition lobe and one amino acid residue, R654, is located in the RuvC-III domain.

The inventors first constructed four modified SaCas9 proteins wherein the modified proteins were single amino acid substitution mutants whereby the wild-type amino acid was substituted with alanine. The single amino acid substitution mutations were in the R245, N413, N419, and R654 positions and the mutants were R245A, N413A, N419A, and R654A, respectively. It was tested whether these mutants showed comparable on-target activities compared to the wild-type (WT) SaCas9 using targeted deep sequencing on three human endogenous sites, EMX1 site 6 (EMX1_6), VEGFA site 8 (VEGFA_8), and EMX1 site 1 (EMX1_1) (FIG. 1d).

The three target sites were selected to assess both of canonical NNGRRT PAM (EMX_6 and VEGFA_8 were both edited at high efficiencies) and a non-canonical NNARRT PAM (EMX1_1) for which about 20% the cleavage efficiency of canonical PAM in an EGFR disruption assay was achieved but which has never been tested on a human endogenous target. These targets are also associated with a substantial number of off-target sites in the human genome and well suited for downstream evaluation of targeting specificity.

Using targeted deep sequencing, the inventors unexpectedly found that all four single SaCas9 mutants (i.e. R245A, N413A, N419A, and R654A) retained comparable on-target activities in comparison to WT SaCas9, ranging from approximately 20%-60% activity across the three human endogenous sites EMX1_6, VEGFA_8, EMX1_1 as shown in FIGS. 1D-1F. At the non-canonical PAM NNARRT endogenous site EMX_1, SaCas9 modified proteins achieved 17-23% indel editing outcome.

Figure 1G:
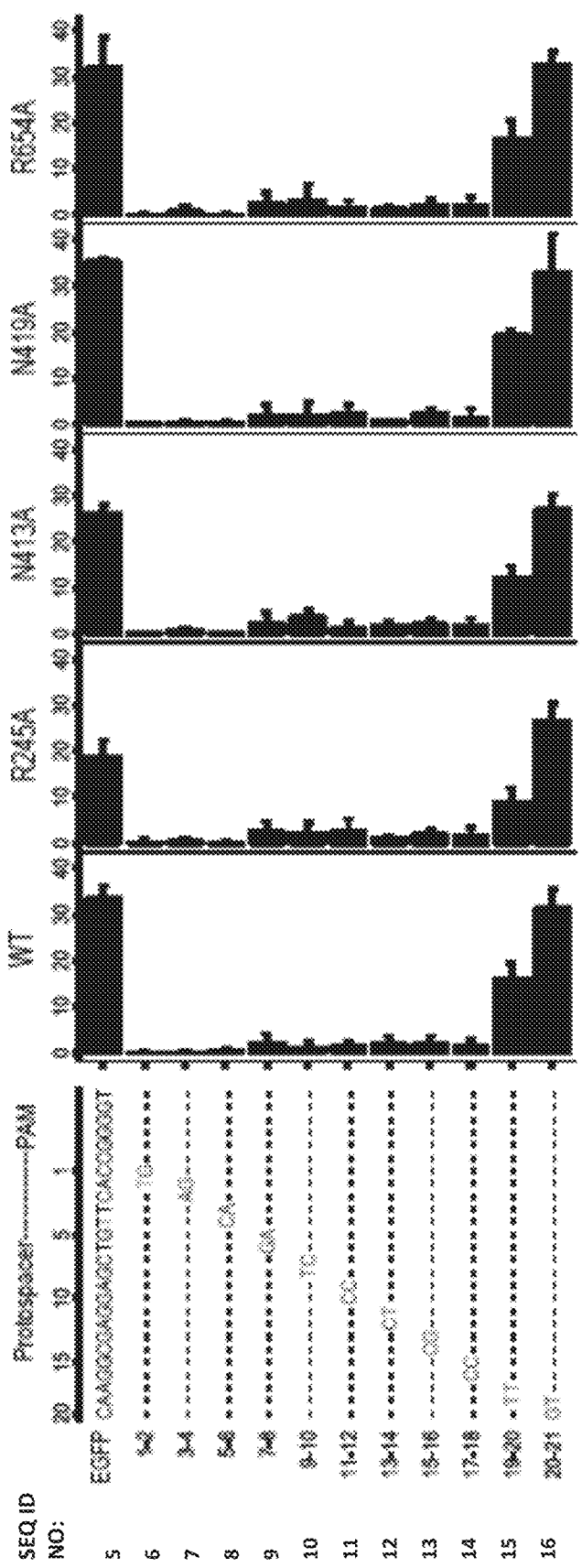
FIG. 1G shows human cell EGFP disruption activities of wild-type SaCas9 (WT) and SaCas9 modified proteins R245A, N413A, N419A and R654A using target protospacer matched or mis-matched gRNA.

The inventors used an EGFP-disruption assay to evaluate SaCas9 cleavage efficiency on expressed eGFP with full-match and tiling 2-base mismatch guide sequences, as illustrated in FIG. 1G. The R245A, N419A and R654A mutants possessed similar cleavage efficacy to the WT-SaCas9. All the SaCas9 proteins tested were highly sensitive to mismatches between guide RNA (gRNA) and the target at the PAM-proximal positions 1 to 6, relatively less sensitive at positions 7 to 18 and insensitive at positions 19 to 21. In the EGFP-disruption assay, no noticeable cleavage difference was observed between WT and the R245A, N413A, N419A, and R654A SaCas9 mutants using the mismatched guides.

Example 2

Genome-Wide Targeting Specificity by the Single Substitution SaCas9 Mutants

Figure 2C:
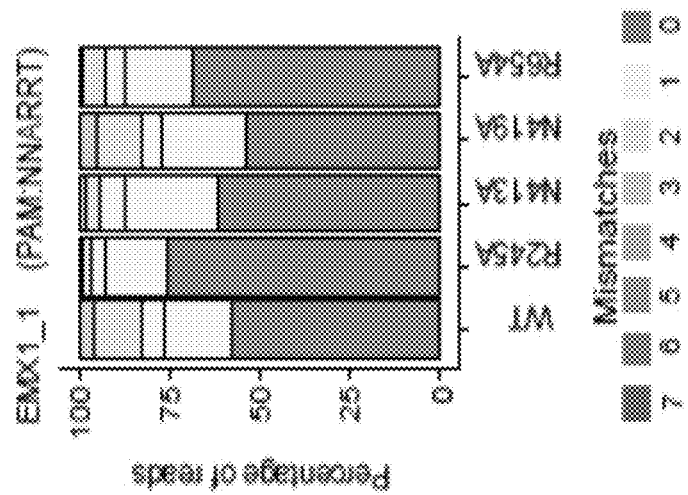
FIG. 2C is a bar graph showing the percentage of edited reads detected by GUIDE-seq at on-target site (green) and off-target sites (ordered by number of mismatches from 1 to 7) among total edited reads by VVT SaCas9 and SaCas9 modified proteins R245A, N413A, N419A and R654A at EMX1_1.
Figure 2B:
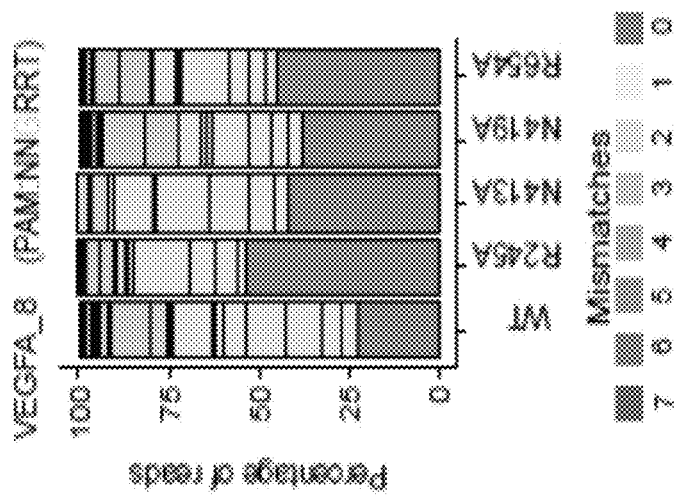
FIG. 2B is a bar graph showing the percentage of edited reads detected by GUIDE-seq at on-target site (green) and off-target sites (ordered by number of mismatches from 1 to 7) among total edited reads by VVT SaCas9 and SaCas9 modified proteins R245A, N413A, N419A and R654A at VEGFA_8.
Figure 2A:
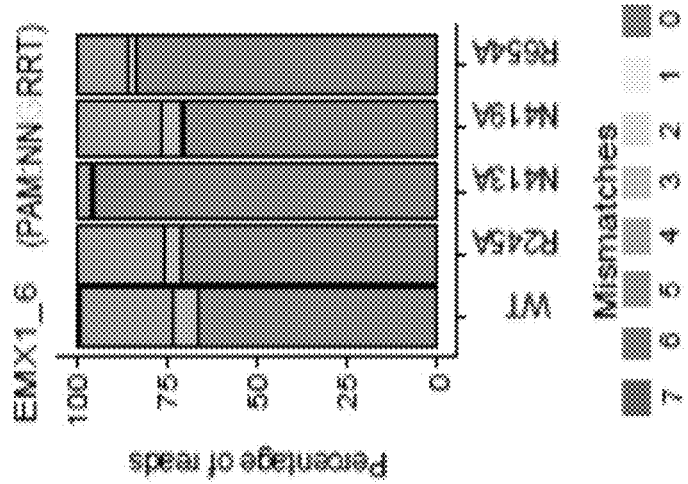
FIG. 2A is a bar graph showing the percentage of edited reads detected by GUIDE-seq at on-target site (green) and off-target sites (ordered by number of mismatches from 1 to 7) among total edited reads by VVT SaCas9 and SaCas9 modified proteins R245A, N413A, N419A and R654A at EMX1_6.
Figure 2D:
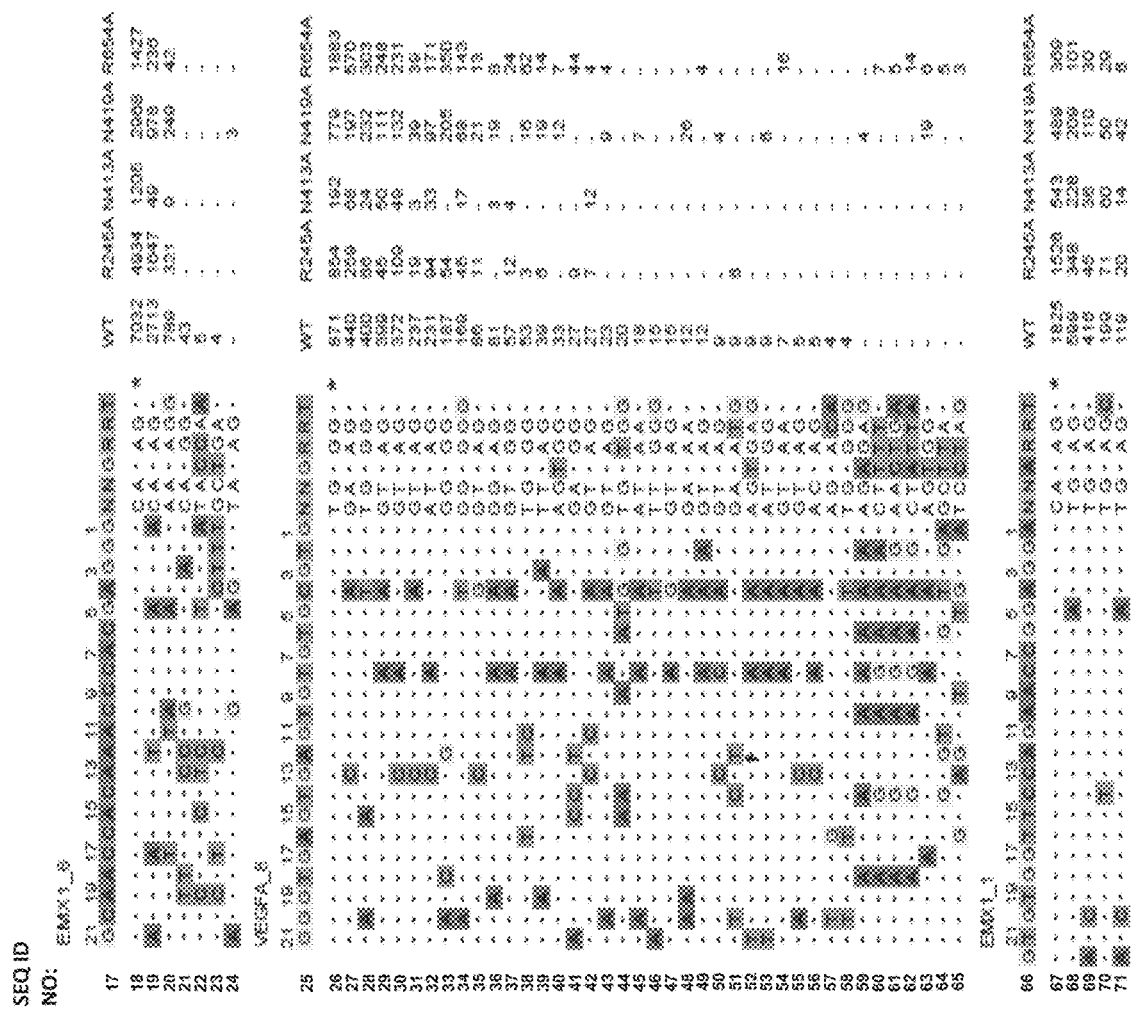
FIG. 2D shows genome-wide cleavage sites detected by GUIDE-Seq on EMX1_6, VEGFA_8 and EMX1_1. Read counts listed on the right represent the number of GUIDE-Seq reads; on-target site is indicated by "*" and mismatched bases in off-target sites with the on-target site are highlighted.

The inventors evaluated genome-wide targeting activity of the R245A, N413A, N419A, and R654A mutants at the EMX1_6, VEGFA_8, EMX1_1 endogenous sites using GUIDE-seq17. With reference to FIGS. 2A, 2B and 2C, it was unexpectedly found that the four single mutants showed improved specificity of varied levels at a canonical PAM (EMX1_6), a known promiscuous (VEGFA_8) site and a non-canonical PAM (EMX1_1) site. As seen in FIG. 2A, the N413A mutant showed significantly higher specificity at EMX1_6 site compared to WT (wildtype). As shown in FIG. 2D, the R245A mutant nearly halved the number of off-target sites at both of the canonical PAM sites, improved on- to off-target read ratio and retained a comparable number of on-target reads (70%, 98% and 84%, respectively, at the three sites) when compared to WT-SaCas9. The other three single mutants, i.e. N413A, N419A, and R654A improved on- to off-target ratio across the three sites.

Example 3

Genome-Wide Targeting Specificity at Expanded Endogenous Sites

To further evaluate SaCas9 mutant genome-wide targeting specificity, the inventors performed GUIDE-seq analyses to include all of the eleven endogenous sites (6 canonical and 5 non-canonical PAMs) previously subjected to GUIDE-seq. A quadruple mutant, i.e. a modified protein containing four amino acid substitutions referred to as SaCas9-HF (with the following four amino acid mutations: R245A, N413A, N419A, and R654A), was generated to test the combined effectiveness of four mutations. The R245A modified protein was also evaluated in view of data showing consistently high on-target cleavage efficiency.

Figure 3A:
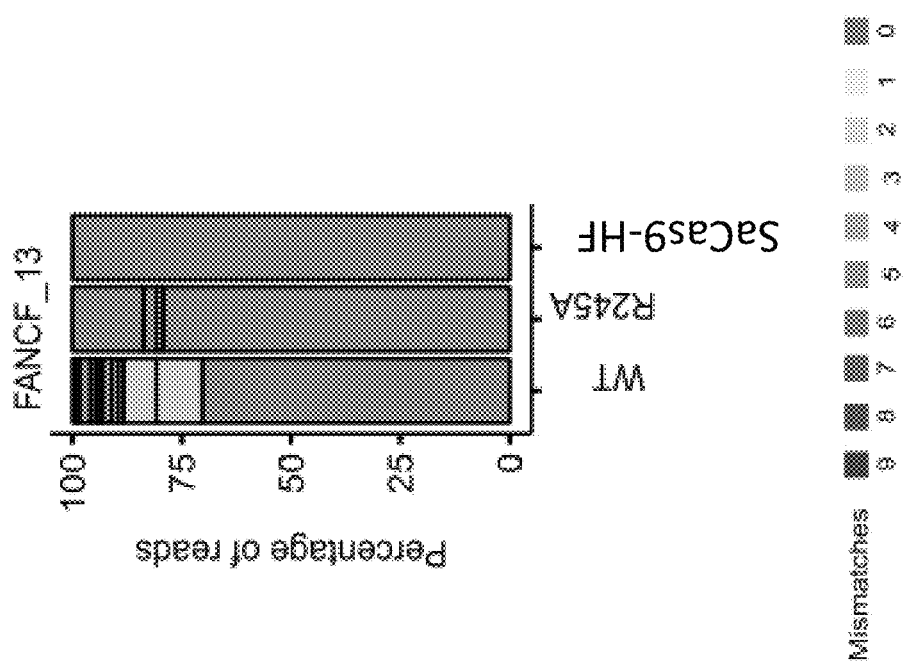
FIG. 3A is a bar graph showing the percentage of edited reads detected by GUIDE-seq at on-target site (green) and off-target sites (ordered by number of mismatches from 1 to 9) by wild-type SaCas9 (WT), SaCas9 modified protein R245A (i.e. with a mutation at position R245), and SaCas9 modified protein HF with mutations at positions R245, N413, N419 and R654A (SaCas9-HF) at FANCF_13, i.e. modified Cas9 protein comprising an amino acid sequence as defined in SEQ ID NO: 3.
Figure 3B:
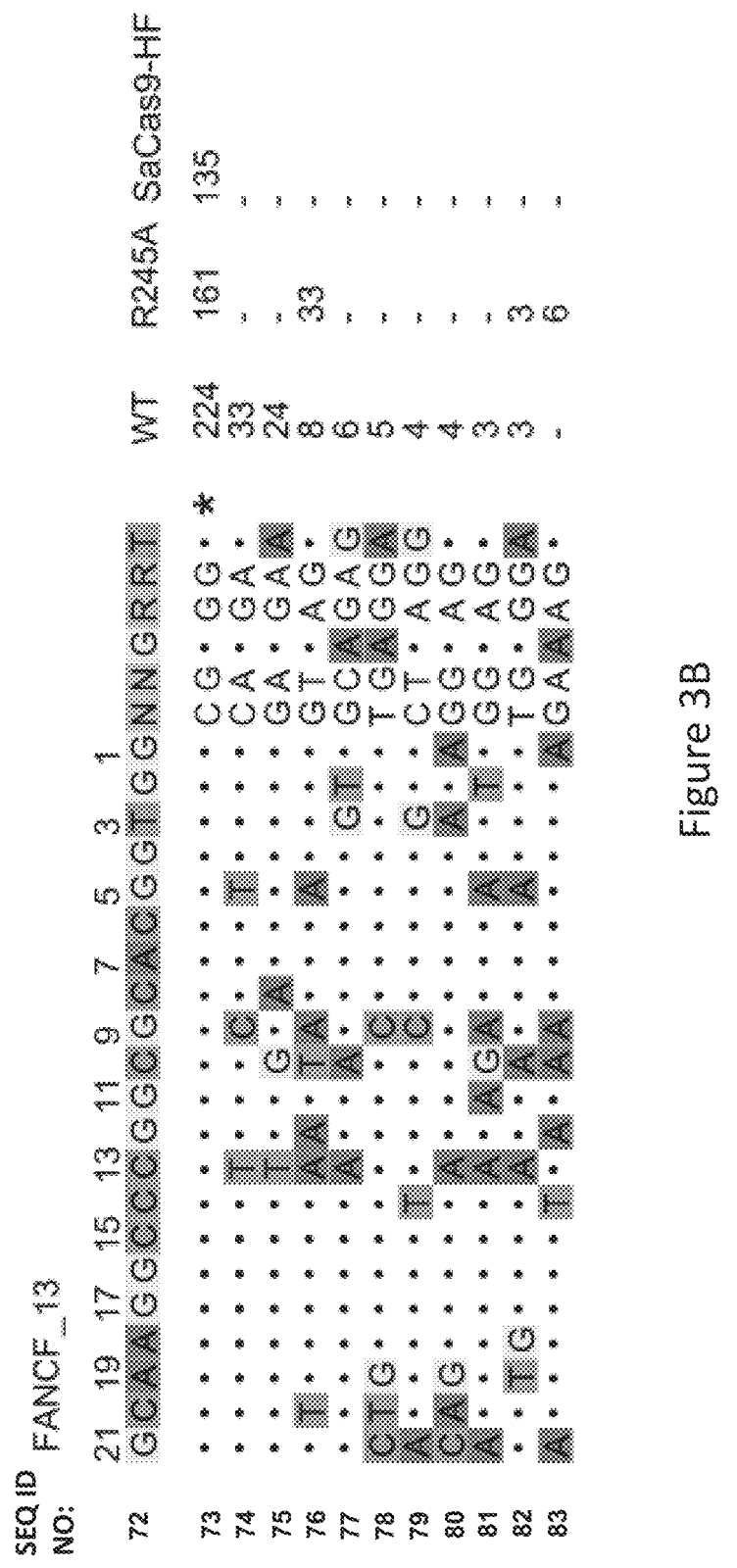
Figure 3C:
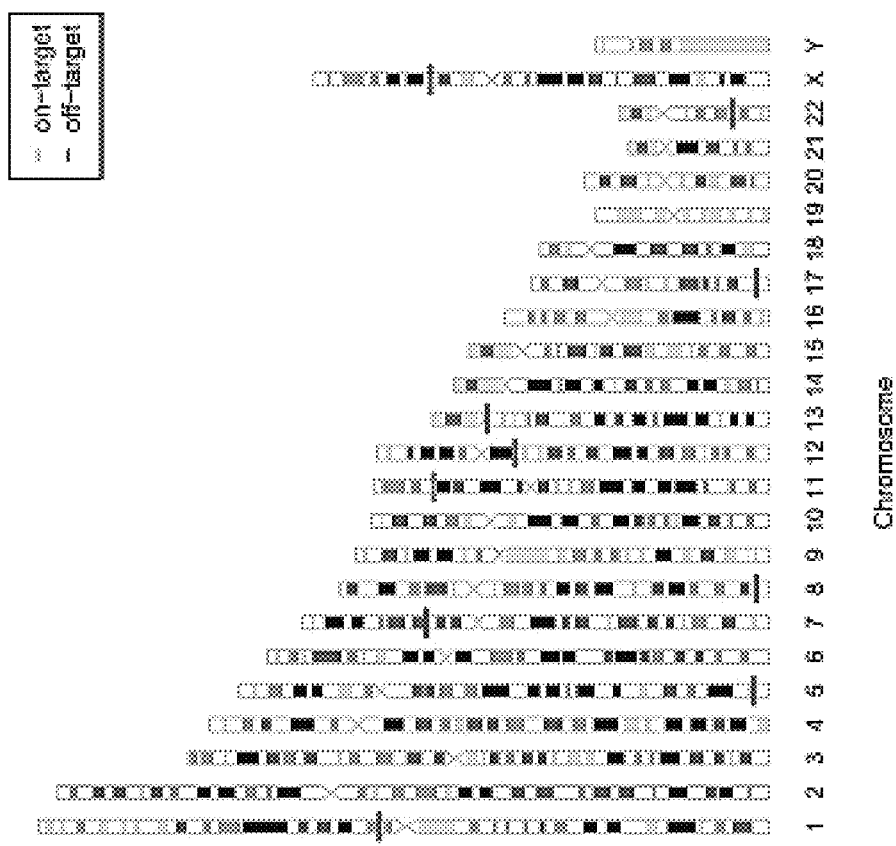
FIG. 3C shows on-target and off-target cleavages detected by GUIDE-Seq of wild-type SaCas9 (WT).
Figure 3D:
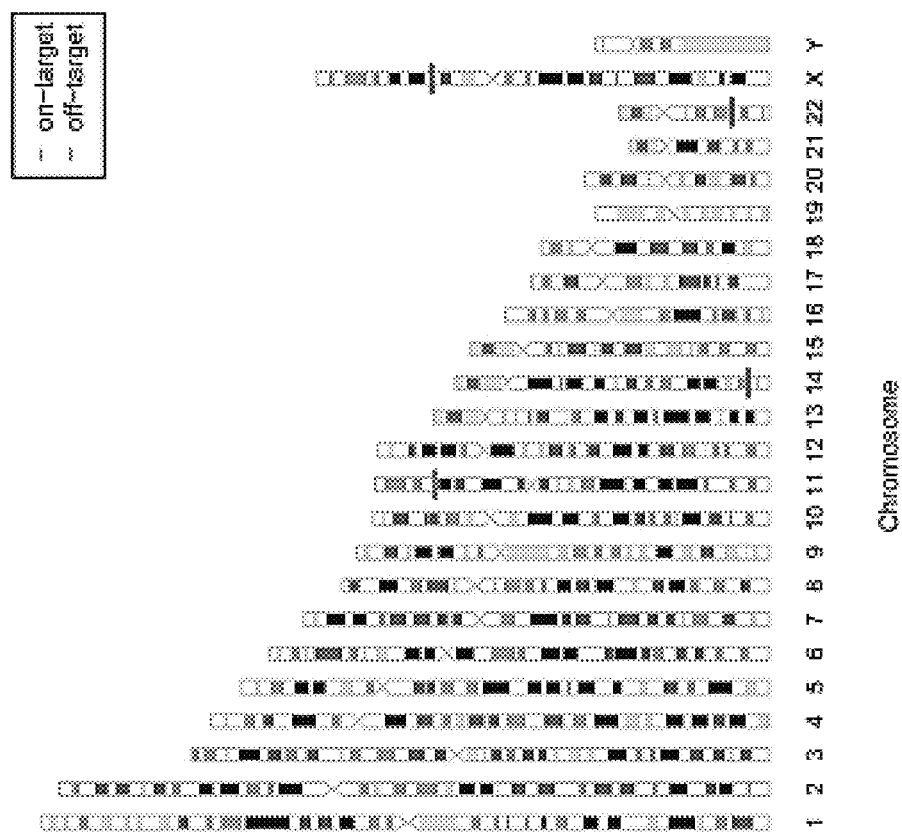
FIG. 3D shows on-target and off-target cleavages detected by GUIDE-Seq of SaCas9 modified protein R245A.
Figure 3E:
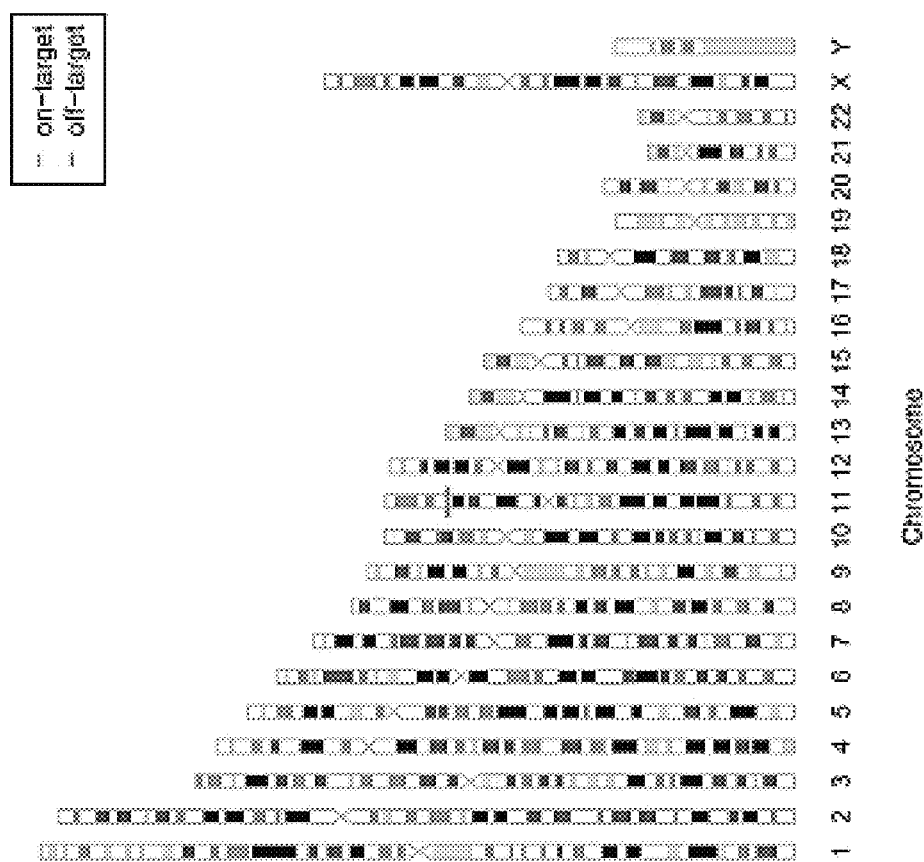
FIG. 3E shows on-target and off-target cleavages detected by GUIDE-Seq of SaCas9 modified protein SaCas9-HF with mutations at positions R245, N413, N419 and R654, i.e. modified Cas9 protein comprising an amino acid sequence as defined in SEQ ID NO: 3.
Figure 3F:
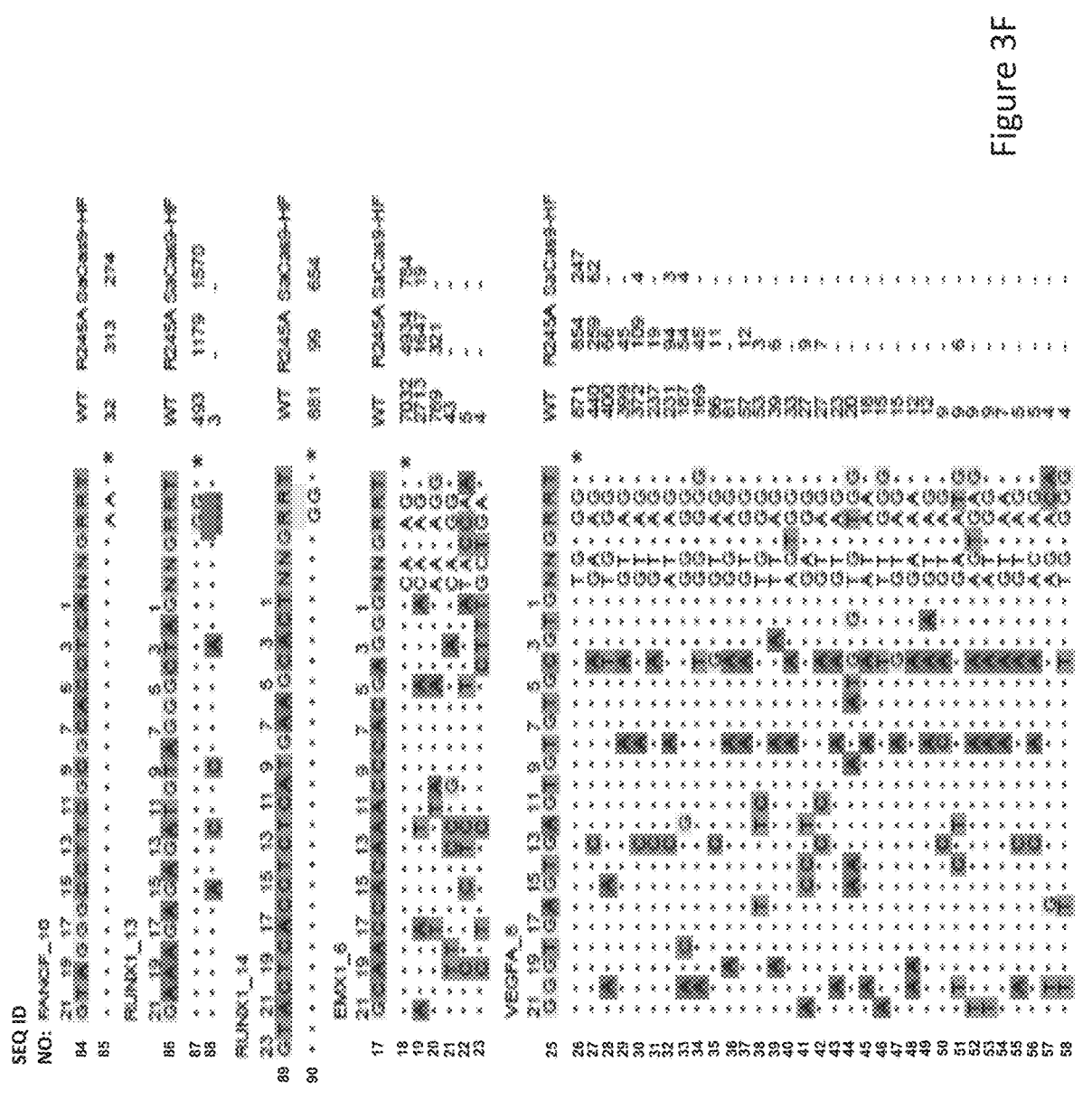

As seen in FIG. 3B, FIG. 3C and FIG. 3F, among the six canonical PAM sites, FANCF_13 showed nine off-target sites by WT-SaCas9 and no detectable off-target sites by SaCas9-HF, illustrating the marked improved specificity of SaCas9-HF in comparison to WT-SaCas9 and improved specificity over the R245A modified protein.

With reference to FIG. 3F, SaCas9-HF showed significant reductions of off-target activity for EMX1_6 and the known promiscuous site VEGFA_8 in comparison to WT-SaCas9 and the R245A mutant. Nearly no off-target activity by WT-SaCas9 was detected for FANCF_10, RUNX1_13 and RUNX1_14. Unexpectedly, SaCas9-HF advantageously achieved about 8.6-, 3.2- and 0.74-fold the GUIDE-Seq reads of WT-SaCas9, respectively, for the three sites. Further, SaCas9-HF showed no cleavage at the sole off-target site when targeting RUNX1_13 by WT-SaCas9.

Figure 3G:
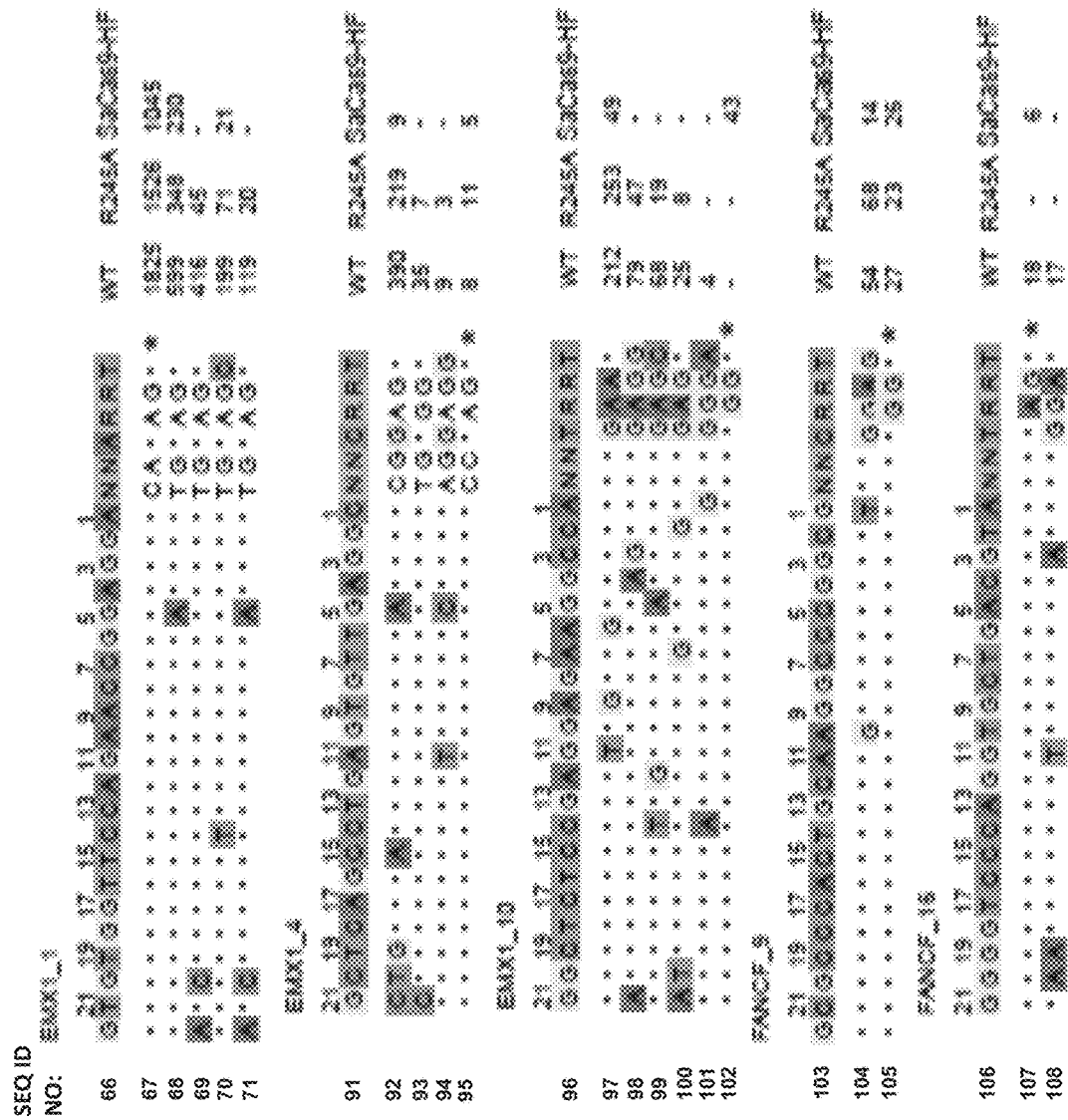
FIG. 3G shows genome-wide cleavage sites detected by GUIDE-Seq at non-canonical NNNRRT PAM sites.

As seen in FIG. 3G, for the five non-canonical PAM sites, 1 to 4 off-target sites were detected for WT-SaCas9 and this was significantly reduced to 0 to 2 for SaCas9-HF. SaCas9-HF also had significantly fewer off-target sites compared to the R245A mutant on EMX1_1, EMX1_4 and EMX1_10. WT-SaCas9 and the R245A mutant had substantial level of activity on EMX1_1 that contains a NNARRT PAM and activity on NNYRRT PAM sites.

Example 4

Epistasis Effect of SaCas9 Residues on Targeting Specificity

The inventors constructed all combinations of modified proteins, i.e. double/triple/quadruple mutants from the four R245A, N413A, N419A, and R654A mutations to test for improved DNA specificity. GUIDE-seq were performed on the modified proteins with one or more mutations of R245A, N413A, N419A, and R654A targeting three endogenous human sites. GUIDE-Seq showed significant improvement by SaCas9-HF (modified protein with mutations of R245A, N413A, N419A, and R654A) at three endogenous sites, namely EMX1_6, VEGFA_8 and FANCF_13.

Figure 4A:
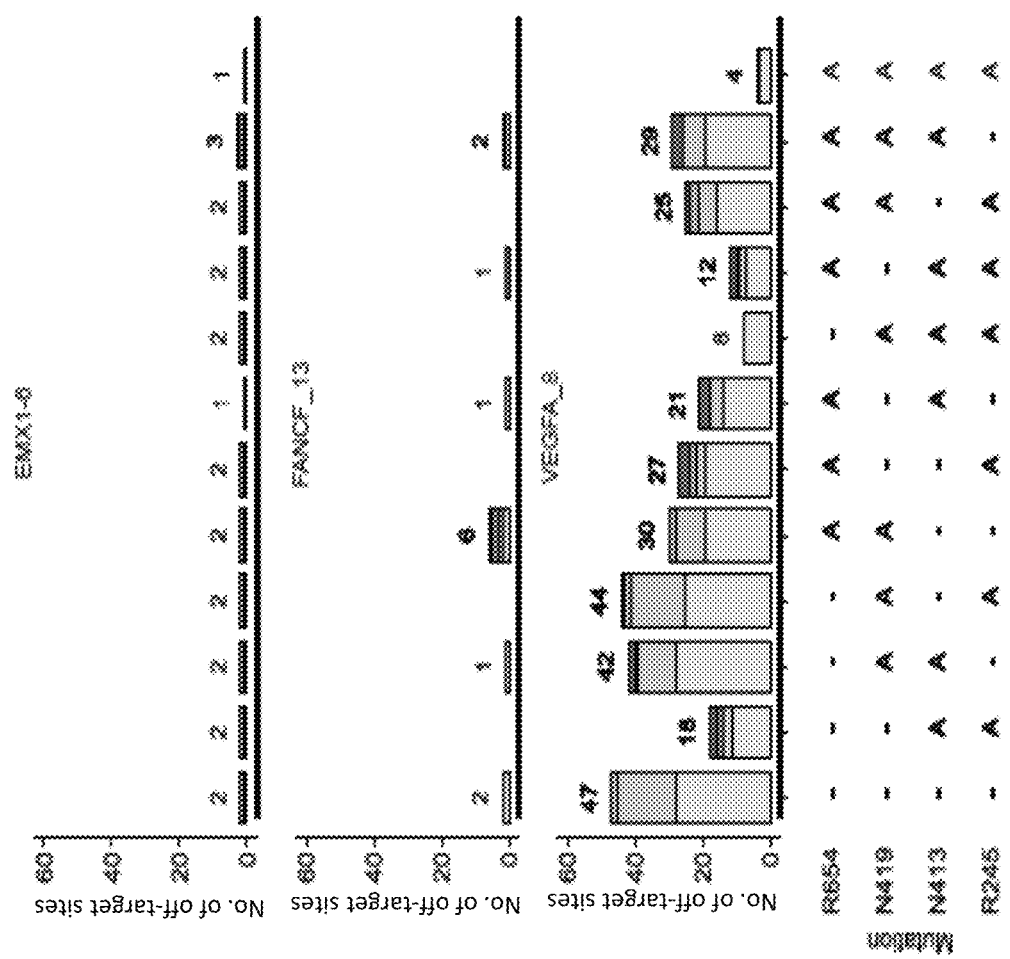
FIG. 4A is a bar graph showing the number of off-target sites identified at EMX1_6, FANCF_13 and VEGFA_8 using GUIDE-Seq by different SaCas9 residue mutation combinations.
Figure 4B:
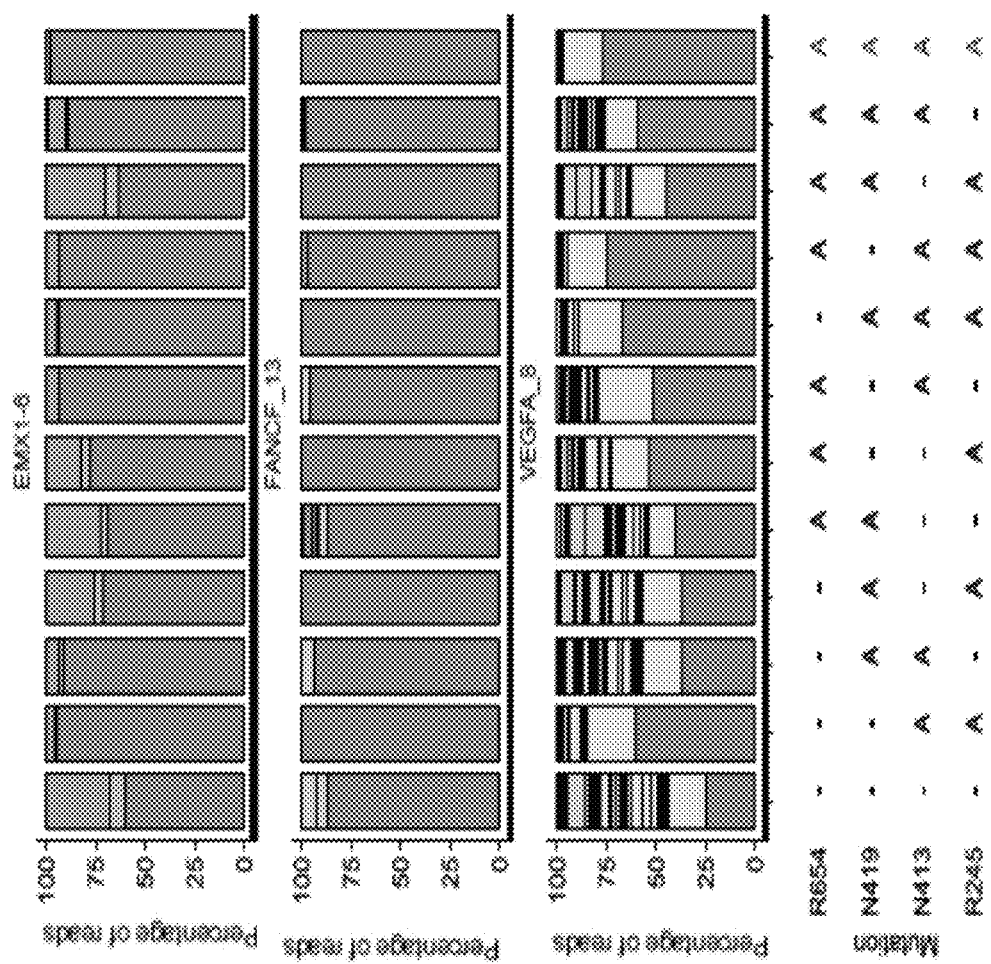
FIG. 4B is a bar graph showing the percentage of edited reads detected by GUIDE-Seq at on-target site (in green) and off-target sites (ordered by the number of mismatches from 1 to 7) among total edited reads by each SaCas9 modified protein.

With reference to FIG. 4A and FIG. 4B, it was found that mutants harboring the R245A, N413A, N419A, and R654A mutations generally had a low number of off-target sites. The modified protein harboring R245A and N413A mutations and the modified protein harboring R245A, N413A, N419A mutations had significantly low off-target activity. Mutation at the N413 position had a significant effect on the number of off-target sites, for example, with reference to FIG. 4A, at VEGFA_8, the modified protein harboring N413A and R245A mutations had significantly lower number of off-target sites compared to the modified protein without a mutation at the N413 position and harboring R245A-N419 mutations. The positive effect of a mutation at the N413 position in reducing the number of off-target sites at VEGFA_8 is also exemplified in FIG. 4A where the modified protein harboring the R245A, N413A, N419A, and R654A mutations, i.e. SaCas9-HF, had a significantly lower number of off-target sites compared to the modified protein harboring R245A, N419A and R654A mutations, i.e. without a mutation at the N413 position, showing the advantageous effect of the mutation at the N413 position in improving specificity of the SaCas9 protein.

Example 5

Improved Specificity on KKH-SaCas9

Figure 5A:
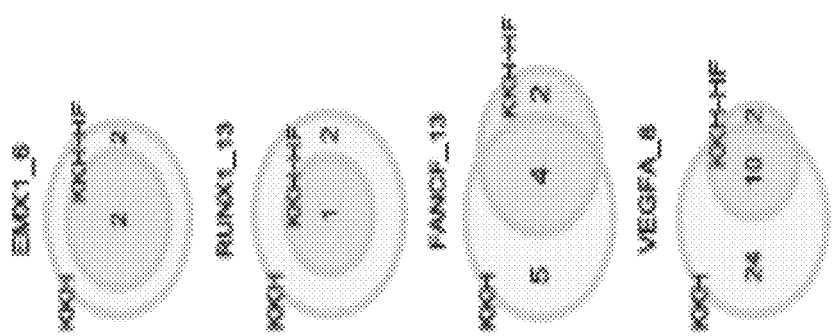
FIG. 5A is a venn diagram comparing the number of off-target sites between a modified protein comprising mutations at E782, N968 and R1015 positions (indicated as "KKH" in the figure) and a modified protein with mutations at E782, N968, R1015, R245, N413, N419 and R654 positions comprising an amino acid sequence as defined in SEQ ID NO: 4 (KKH-SaCas9-HF, indicated as KKH-HF in the figure) when targeting six sites including EMX1_6, RUNX1_13, RUNX1_14, FANCF_10, FANCF_13, VEGFA_8 with canonical NNGRRT PAM.
Figure 5B:
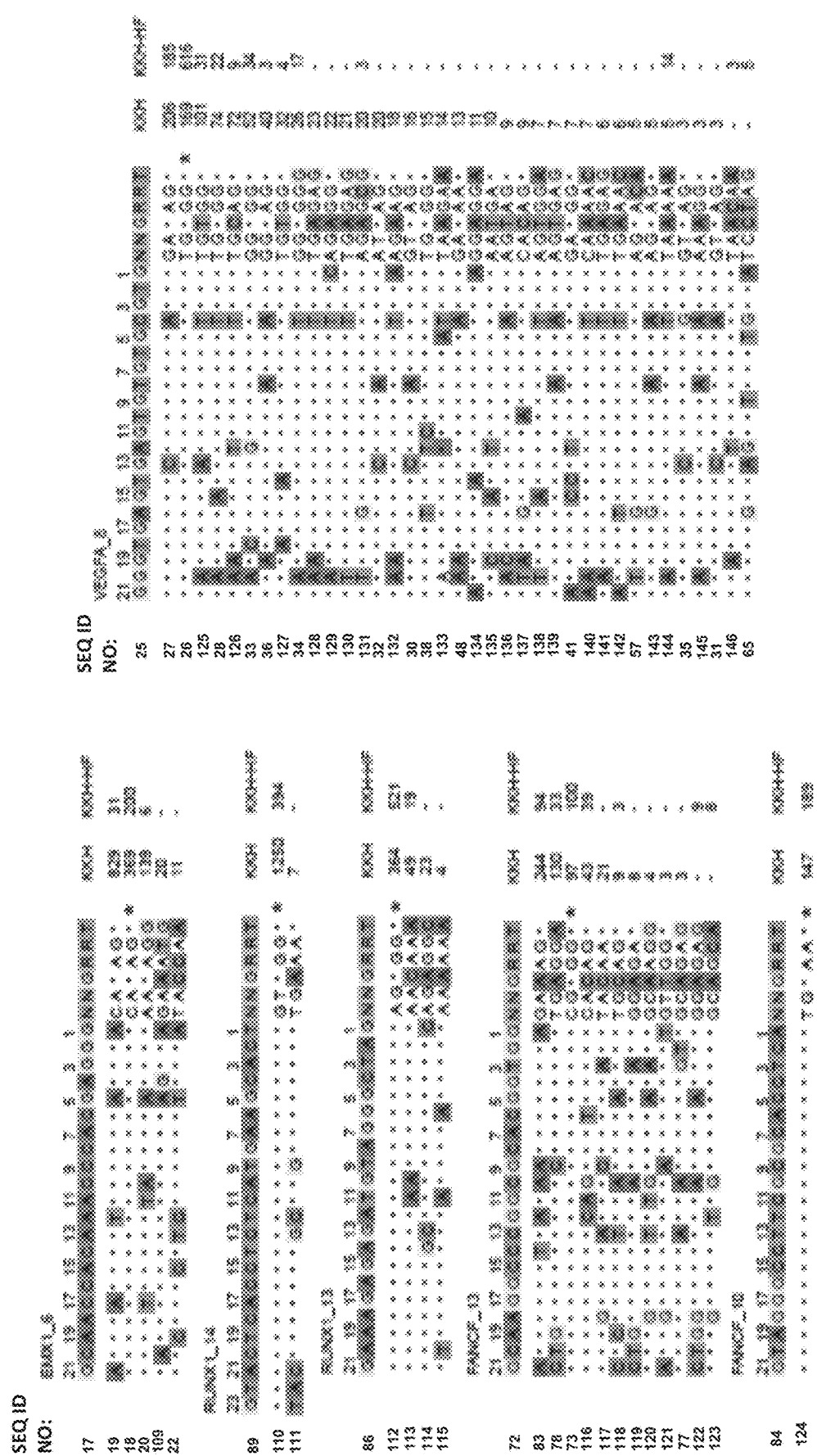
FIG. 5B shows GUIDE-Seq detected cleavage sites by a modified protein comprising mutations at E782, N968 and R1015 positions (indicated as "KKH" in the figure) and a modified protein with mutations at E782, N968, R1015, R245, N413, N419 and R654 positions comprising an amino acid sequence as defined in SEQ ID NO: 4 (KKH-SaCas9-HF, indicated as "KKH-HF" in the figure) when targeting six sites with canonical NNGRRT PAM. Read counts listed on the right represent the number of GUIDE-Seq reads. On-target site is indicated with "*". Mismatched bases in off-target sites with the on-target site are highlighted.
Figure 5C:
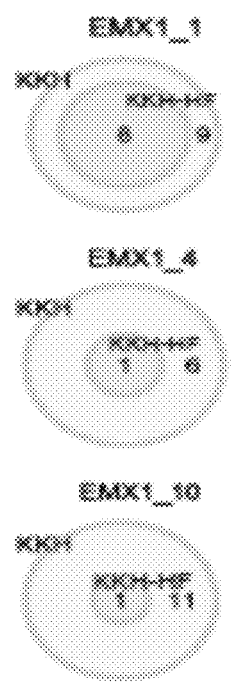
FIG. 5C is a venn diagram comparing the number of off-target sites between a modified protein comprising mutations at E782, N968 and R1015 positions (indicated as "KKH" in the figure) and a modified protein with mutations at E782, N968, R1015, R245, N413, N419 and R654 positions comprising an amino acid sequence as defined in SEQ ID NO: 4 (KKH-SaCas9-HF, indicated as "KKH-HF" in the figure) when targeting five sites including EMX1_1, EMX1_4, EMX1_10, FANCF_9 and FANCF_16 with non-canonical NNNRRT PAM.
Figure 5D:
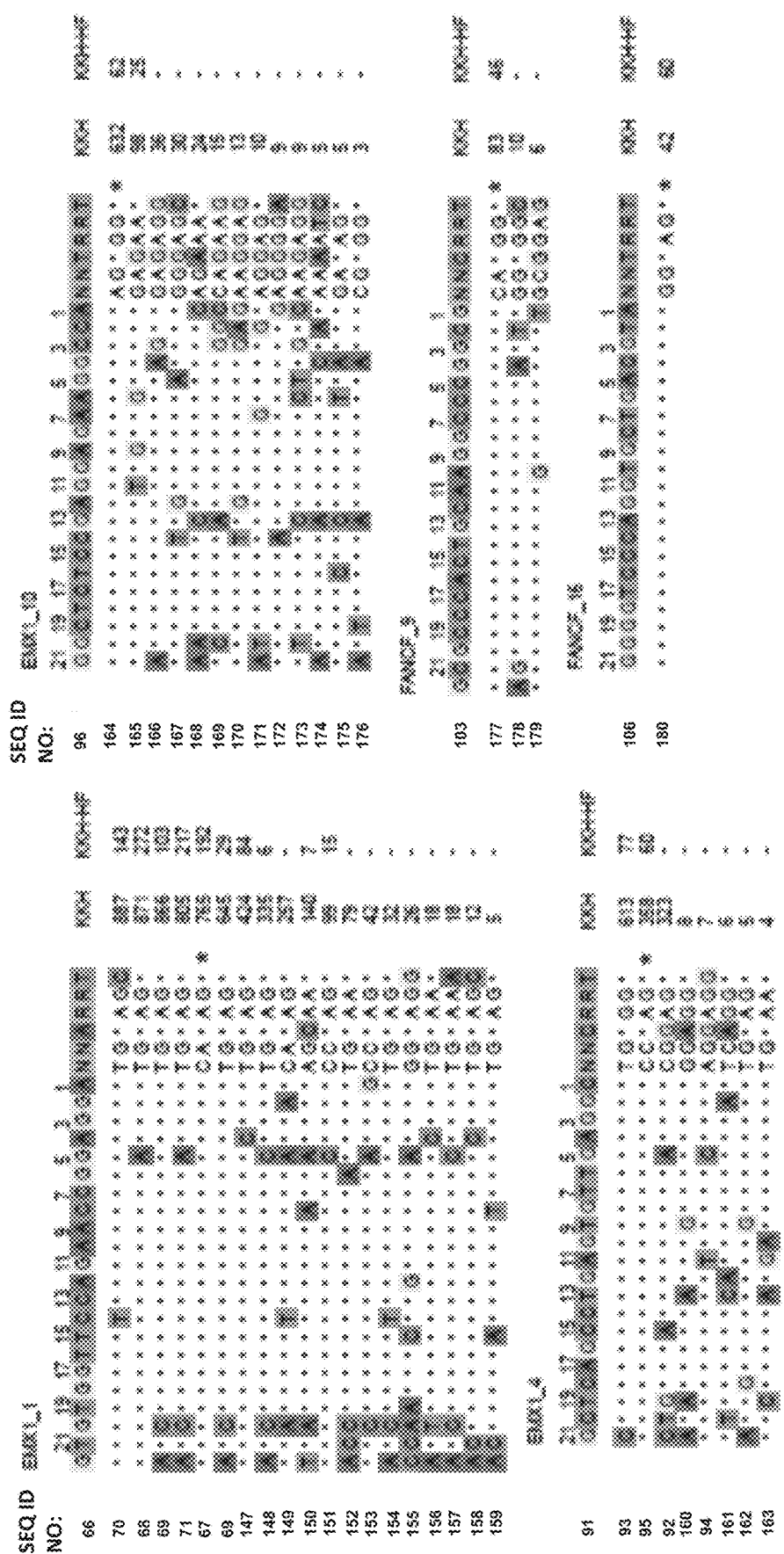
FIG. 5D shows GUIDE-Seq detected cleavage sites by a modified protein comprising mutations at E782, N968 and R1015 positions (indicated as "KKH" in the figure) and a modified protein with mutations at E782, N968, R1015, R245, N413, N419 and R654 positions comprising an amino acid sequence as defined in SEQ ID NO: 4 (KKH-SaCas9-HF, indicated as "KKH-HF" in the figure) when targeting six sites with non-canonical NNNRRT PAM. Read counts listed on the right represent the number of GUIDE-Seq reads. On-target site is indicated with "*". Mismatched bases in off-target sites with the on-target site are highlighted.

The inventors tested the targeting specificity of a modified protein with mutations of R245A, N413A, N419A, R654A, E782K, N968K and R1015H (referred to as KKH-SaCas9-HF, i.e. the modified protein comprising an amino acid sequence as defined by SEQ ID NO: 2) and compared this with an SaCas9 variant with mutations of E782K, N968K and R1015H at all of the eleven endogenous target sites (6 containing canonical PAM of WT-SaCas9 and 5 containing KKH targeting PAM) using GUIDE-Seq as shown in FIGS. 5B and 5D. It was found that KKH-SaCas9-HF had enhanced targeting specificity and significantly reduced the number of off-target sites (FIG. 5A) whilst increasing on-target cleavage frequency at four canonical PAM sites (FIG. 5A and FIG. 5B). With reference to FIG. 5C, KKH-SaCas9-HF significantly reduced the number of off-target sites compared to the SaCas9 variant with mutations of E782K, N968K and R1015H.

The inventors sought to test their hypothesis of improving the targeting accuracy of SaCas9 by modifying amino acid residues in close polar contact with the gRNA-target DNA interface in the PAM-distal region. Using GUIDE-Seq (genome-wide unbiased identification of double-stranded breaks enabled by sequencing), it was found that one engineered modified SaCas9 protein, SaCas9-HF (with mutations of N413A,R245A,N419A and R654A) advantageously and significantly reduced off-target cleavages without compromising on-target activity. Of five endogenous target sites in human cells tested using SaCas9-HF, significantly less or no off-target activity was detected at the target sites. Further, adding these residue modifications onto the KKH-SaCas9 variant previously described (i.e. with mutations of E782K, N968K and R1015H) to target a broader PAM range (NNNRRT) also resulted in significantly reduced off-target activity of KKH-SaCas9-HF when compared with KKH-SaCas9 across endogenous target sites in human cells tested. Thus, the present invention provides an improved modified SaCas9 protein for use in altering the genome of a cell with increased specificity enabling genome-editing applications with high genome-wide precision.

---

The invention claimed is:

1. A modified *Streptococcus aureus* Cas9 protein with a mutation at an N413 position, and optionally one or more of a nuclear localization sequence, a cell penetrating peptide sequence, an affinity tag or a fusion base editor protein, wherein the modified protein comprises the amino acid sequence selected from SEQ ID NO: 1, SEQ ID NO: 2, SEQ ID NO: 3, SEQ ID NO: 4 or a homologue thereof having at least 90% overall sequence identity to the amino acid sequence.

2. The modified protein of claim 1, wherein the modified protein comprises the amino acid sequence of SEQ ID NO: 1.

3. The modified protein of claim 1, wherein the modified protein comprises the amino acid sequence of SEQ ID NO: 2.

4. The modified protein of claim 1, further comprising one or more mutations at R245, N419 or R654 positions.

5. The modified protein of claim 1, wherein the modified protein comprises the amino acid sequence of SEQ ID NO: 3.

6. The modified protein of claim 3, further comprising mutations at R245, N419 and R654 positions.

7. The modified protein of claim 1, wherein the modified protein comprises the amino acid sequence of SEQ ID NO: 4.

8. The modified protein of claim 1, wherein the modified protein with optionally at least one additional mutation selected from the group consisting of R245, N419 and R654 positions decreases nuclease activity at one or more sites on a target DNA molecule.

9. The modified protein of claim 8, wherein the one or more sites are off-target sites on the target DNA molecule.

10. The modified protein of claim 1, wherein the mutation is a single amino acid substitution.

11. An in vitro method for altering the genome of an isolated host cell, the method comprising the step of using a modified *Streptococcus aureus* Cas9 protein with a mutation at an N413 position, and optionally one or more of a nuclear localization sequence, a cell penetrating peptide sequence, an affinity tag or a fusion base editor protein, wherein the modified protein comprises the amino acid sequence selected from SEQ ID NO: 1, SEQ ID NO: 2, SEQ ID NO: 3, SEQ ID NO: 4 or a homologue thereof having at least 90% overall sequence identity to the amino acid sequence.

12. The method of claim 11, wherein the modified protein is expressed in the cell or the cell is contacted with the modified protein and a guide RNA having a region complementary to a selected portion of the genome of the cell.

13. The method of claim 11, wherein the modified protein comprises the amino acid sequence of SEQ ID NO: 1.

14. The method of claim 11, wherein the modified protein comprises the amino acid sequence of SEQ ID NO: 2.

15. The method of claim 11, wherein the modified protein further comprises one or more mutations at R245, N419 or R654 positions.

16. The method of claim 11, wherein the modified protein comprises an amino acid sequence of SEQ ID NO: 3.

17. The method of claim 14, wherein the modified protein further comprises one or more mutations at R245, N419 and R654 positions.

18. The method of claim 11, wherein the modified protein comprises the amino acid sequence of SEQ ID NO: 4.

19. The method of claim 11, wherein the modified protein with optionally at least one additional mutation selected from the group consisting of R245, N419 and R654 positions decreases nuclease activity at one or more off-target sites on a target DNA molecule of the cell.

20. The method of claim 11, wherein the mutation is a single amino acid substitution.

21. A kit comprising a modified *Streptococcus aureus* Cas9 protein with a mutation at an N413 position, and optionally one or more of a nuclear localization sequence, a cell penetrating peptide sequence, an affinity tag or a fusion base editor protein, wherein the modified protein comprises the amino acid sequence selected from SEQ ID NO: 1, SEQ ID NO: 2, SEQ ID NO: 3, SEQ ID NO: 4 or a homologue thereof having at least 90% overall sequence identity to the amino acid sequence.

22. The kit of claim 21, wherein the modified protein comprises the amino acid sequence of SEQ ID NO: 1.

23. The kit of claim 22, wherein the modified protein comprises the amino acid sequence of SEQ ID NO: 2.

24. The kit of claim 21, the modified protein further comprising one or more mutations at R245, N419 or R654 positions.

25. The kit of claim 23, the modified protein further comprising one or more mutations at R245, N419 and R654 positions.

26. The kit of claim 23, wherein the modified protein comprises the amino acid sequence of SEQ ID NO: 3.

27. The kit of claim 23, wherein the modified protein comprises the amino acid sequence of SEQ ID NO: 4.

28. The kit of claim 23, wherein the modified protein comprising optionally at least one additional mutation selected from the group consisting of R245, N419 and R654 decreases nuclease activity at one or more off-target sites on a target DNA molecule.

* * * * *